(12) United States Patent
Breyer et al.

(10) Patent No.: US 8,389,222 B2
(45) Date of Patent: Mar. 5, 2013

(54) APOLIPOPROTEIN FINGERPRINTING TECHNIQUE AND METHODS RELATED THERETO

(75) Inventors: Emelita De Guzman Breyer, Tucker, GA (US); Mary K. Robinson, Decatur, GA (US)

(73) Assignees: Emelita D. Breyer, Tucker, GA (US); Sean M. Breyer, Tucker, GA (US)

( * ) Notice: Subject to any disclaimer, the term of this patent is extended or adjusted under 35 U.S.C. 154(b) by 536 days.

(21) Appl. No.: 12/236,417

(22) Filed: Sep. 23, 2008

(65) Prior Publication Data
US 2009/0155812 A1 Jun. 18, 2009

Related U.S. Application Data

(63) Continuation-in-part of application No. PCT/US2007/007359, filed on Mar. 23, 2007.

(60) Provisional application No. 60/743,678, filed on Mar. 23, 2006.

(51) Int. Cl.
*G01N 33/53* (2006.01)
(52) U.S. Cl. ......................... 435/7.1; 436/518
(58) Field of Classification Search .................. None
See application file for complete search history.

(56) References Cited

U.S. PATENT DOCUMENTS

| | | | |
|---|---|---|---|
| 5,510,342 A * | 4/1996 | Washburn et al. ............ | 514/179 |
| 6,753,185 B2 | 6/2004 | Macfarlane et al. | |
| 7,776,550 B2 * | 8/2010 | Block et al. ..................... | 435/7.1 |
| 7,781,219 B2 * | 8/2010 | Hazen et al. ..................... | 436/86 |
| 2001/0025157 A1 * | 9/2001 | Kriesell ........................ | 604/132 |
| 2005/0032761 A1 * | 2/2005 | Morton et al. ................. | 514/177 |
| 2005/0048547 A1 | 3/2005 | Zhao et al. | |
| 2005/0064511 A1 | 3/2005 | Buechler et al. | |
| 2005/0153360 A1 | 7/2005 | Hochstrasser et al. | |
| 2005/0271653 A1 * | 12/2005 | Strahilevitz ................ | 424/140.1 |
| 2005/0272095 A1 * | 12/2005 | Wang ............................. | 435/7.1 |
| 2006/0233902 A1 * | 10/2006 | Yajima et al. .................. | 424/778 |
| 2007/0042425 A1 | 2/2007 | Hochstrasser et al. | |
| 2007/0054407 A1 * | 3/2007 | Chen et al. ....................... | 436/86 |
| 2007/0166758 A1 | 7/2007 | Lescuyer et al. | |
| 2007/0178438 A1 * | 8/2007 | Chatterjee et al. ................ | 435/4 |

OTHER PUBLICATIONS

Levels et al. (Proteome Science 2007 5:15).*
Dayal et al. (J. Proteome Research 2002 vol. 1, p. 375-380).*
Malik et al. (Clinical Cancer Research 2005 vol. 11, p. 1073-1085).*
Wang et al. (J. Biological Chem. 1999 vol. 274, p. 1814-1820).*
Terrisse et al. (J. Neurochem 1998 vol. 71, p. 1643-1650).*
Beghin, L., et al., Measurement of Apolipoprotein B Concentration in Plasma Lipoproteins by Combining Selective Precipitation and Mass Spectrometry, J. Lipid Res., Jul. 2000, pp. 1172-1176, vol. 41, No. 7.
Blackett, P. R., et al., Apolipoprotein C-III Bound to Apolipoprotein B-Containing Lipoproteins in Obese Girls, Clinical Chemistry, 2003, pp. 303-306, vol. 49, No. 2.
Bondarenko, P.V., et al., Mass Spectral Study of Polymorphism of the Apolipoproteins of Very Low Density Lipoprotein, Journal of Lipid Research, 1999, pp. 543-555, vol. 40.
Chen, et al., Antiandrogenic Therapy Can Cause Coronary Arterial Disease, International Journal of Urology, Oct. 2005, pp. 886-891, vol. 12, No. 10.
Chen, Wen, et al., Proteomic Comparison Between Human Young and Old Brains By Two-Dimensional Gel Electrophoresis and Identification of Proteins, Int. J. Dev. Neurosci., Jun. 2003, pp. 209-216, vol. 21, No. 4.
Choe, Leila H., et al., Apolipoprotein E and Other Cerebrospinal Fluid Proteins Differentiate Ante Mortem Variant Creutzfeldt-Jakob Disease from Ante Mortem Sporadic Creutzfeldt-Jakob Disease, Electrophoresis, Jul. 2002, pp. 2242-2246, vol. 23, No. 14.
Choi, Joungil, et al., Proteomic Identification of Specific Oxidized Proteins in ApoE-Knockout Mice: Relevance to Alzheimer's Disease, Free Radic. Biol. Med., May 1, 2004, pp. 1155-1162, vol. 36, No. 9.
Christen, Y., Oxidative stress and Alzheimer disease, American Journal of Clinical Nutrition, Feb. 2000, pp. 621S-629S, vol. 71, No. 2.
Curry, M.D., et al., Determination of Apolipoprotein A and Its Constitutive A-1 and A-II Polypeptides by Separate Electroimmunoassays, Clin. Chem., 1976, pp. 315-322, vol. 22, No. 3.
Curry, M.D., et al., Determination of Human Apolipoprotein E by Electro-Immunoassay, Biochimica et Biophysica Acta, Jan. 12, 1976, pp. 413-425, vol. 439.
Curry, M.D., et al., Electroimmunoassay, Radioimmunoassay, and Radial Immunodiffusion Assay Evaluated for Quantification of Human Apolipoprotein B, Clinc. Chem., 1978, pp. 280-286, vol. 24, No. 2.
Curry, M.D., et al., Quantitative Determination of Human Apolipoprotein C-III by Electroimmunoassay, Biochimica et Biophysica Acta, 1980, pp. 503-513, vol. 617.
Dahlback, et al., Apolipoprotein M—A Novel Player in High-Density Lipoprotein Metabolism and Atherosclerosis, Current Opinion in Lipidology, Jun. 2006, pp. 291-295, vol. 17, No. 3.
Dallinga-Thie, et al. Plasma apolipoprotein A5 and triglycerides in type 2 diabetes; Diabetologia, 49(7):1505-11, Jul. 2006.
Davidsson, et al., A proteomic study of the apolipoproteins in LDL subclasses in patients with the metabolic syndrome and type 2 diabetes; Journal of Lipid Research, Sep. 2005, 46(9):1999-2006.
Davidsson, Pia, et al., The Use of Proteomics in Biomarker Discovery in Neurodegenerative Diseases, Dis. Markers, 2005, pp. 81-92, vol. 21, No. 2.
De Sain-Van Der Velden, M.G., et al., In Vivo Determination of Very-Low-Density Lipoprotein-Apolipoprotein B100 Secretion Rates in Humans with a Low Dose of L-[1-13 Cavaline] Valine and Isotope Ratio Mass Spectrometry, Anal. Biochem., Dec. 15, 1998, pp. 308-312, vol. 265, No. 2.
Dubrovsky, et al. Clinical Chemistry, 45(9):1675. 1999. Immobilization of monolayers of Fc-binding Receptors on Planar Solid Supports.

(Continued)

*Primary Examiner* — Jacob Cheu

(57) ABSTRACT

A method for determining the concentration and modifications of apolipoprotein in biological samples including plasma, serum, and lipoprotein fractions, by obtaining a sample from a patient, adding a specific volume of an internal standard to the sample, applying the sample to a surface-enhanced, Protein G-coated, antibody-bound chip and removing unbound sample components, analyzing the sample by mass spectrometry, determining the concentration of the apolipoprotein using values of internal standards, and evaluating the concentration of the apolipoprotein, its isoforms, amino acid substitutions and modifications for use as a tool for diagnosing cancer, diabetes, stroke, stress, Alzheimer's disease, inflammation, neurological disease and cardiovascular diseases.

32 Claims, 14 Drawing Sheets

OTHER PUBLICATIONS

Farwig, Zachly N., Analysis of High-Density Lipoprotein Apolipoproteins Recovered From Specific Immobilized pH Gradient Gel pl Domains by Matrix-Assisted Laser Desorption/Ionization Time-of-Flight Mass Spectrometry, Anal. Chem., Aug. 1, 2003, pp. 3823-3830, vol. 75, No. 15.

Favrot, et al. Study of blood lipids in 30 children with malignant hematological disease or carcinoma; Biomedicine & Pharmacotherapy, 38(1):55-9, 1984.

Feingold, et al., Infection and inflammation Decrease Apolipoprotein M Expression, Atherosclerosis, Jul. 2008, pp. 19-26, vol. 199, No. 1.

Florez, H., et al., Increased Apolipoprotein C-III Levels Associated with Insulin Resistance Contribute to Dyslipidemia in Normoglycemic and Diabetic subjects from a Triethnic Population, Atherosclerosis, Sep. 2006, pp. 134-141, vol. 188, No. 1.

Gerber, Y., et al., Association Between Serum Apolipoprotein CII Concentration and Coronary Heat Disease, Preventive Medicine, 2002, pp. 42-47, vol. 35.

Gervaise, et al., Triglycerides, Apo C3 and Lp B:C3 and Cardiovascular Risk in Type II Diabetes, Diabetologia, Jun. 2000, pp. 703-708, vol. 43, No. 6.

Ghafouri, Bijar, et al., Mapping of Proteins in Human Saliva Using Two-Dimensional Gel Electrophoresis and Peptide Mass Fingerprinting, Proteomics, Jun. 2003, pp. 1003-1015, vol. 3, No. 6.

Ghafouri, Bijar, et al., Newly Identified Proteins in Human Nasal Lavage Fluid from Non-Smokers and Smokers Using Two-Dimensional Gel Electrophoresis and Peptide Mass Fingerprinting, Proteomics, Jan. 2002, pp. 112-120, vol. 2, No. 1.

Ghebranious, Nader, et al., Detection of ApoE E2, E3 and E4 Alleles Using MALDI-TOF Mass Spectrometry and the Homogeneous Mass-Extend Technology, Nucleic Acids Res., 2005, pp. e149, vol. 33, No. 17.

Gibb, G.M., et al., Differential Effects of Apolipoprotein E Isoforms On Phosphorylation at Specific Sites on Tau by Glycogen Synthase Kinase-3 Beta Identified by Nano-Electrospray Mass Spectrometry, FEBS Lett, Nov. 24, 2000, pp. 99-103, vol. 485, No. 2-3.

Han, X., et al., Plasmalogen Deficiency in Early Alzheimer's Disease Subjects and In Animal Models: Molecular Characterization Using Electrospray Ionization Mass Spectrometry, J. Neurochem., May 2001, pp. 1168-1180, vol. 77, No. 4.

Hanson, Charlotte L., et al., Phospholipid Complexation and Association with Apolipoprotein C-II: Insights from Mass Spectrometry, Biophys. J., Dec. 2003, pp. 3802-3812, vol. 85, No. 6.

He, Qing-Yu, et al., Serum Biomarkers of Hepatitis B Virus Infected Liver Inflammation: A Proteomic Study, Proteomics, May 2003, pp. 666-674, vol. 3, No. 5.

Hesse, C., et al., Identification of the Apolipoprotein E4 Isoform in Cerebrospinal Fluid with Preparative Two-Dimensional Electroporesis and Matrix-Assisted Laser Desorption-Ionization-Time of Flight Mass Spectrometry, Electrophoresis, May 2001, pp. 1834-1837, vol. 22, No. 9.

Huang, et al., Apolipoprotein M Likely Extends its Anti-Atherogenesis Via Anti-Inflammation, Medical Hypotheses, 2007, pp. 136-140, vol. 69, No. 1.

Hwang, In Kwan, et al., A Proteomic Approach to Identify Substrates of Matrix Metalloproteinase-14 in Human Plasma, Biochim. Biophys. Acta., Oct. 1, 2004, pp. 79-87, vol. 1702, No. 1.

Ito, Y., et al., Apolipoprotein C-IIIo Lacks Carbohydrate Residues: Use of Mass Spectrometry to Study Apolipoprotein Structure, Journal of Lipid Research, 1989, pp. 1781-1787, vol. 30.

Jain, A.K., et al., Statistical Pattern Recognition: A Review, IEEE Transactions on Pattern Analysis and Machine Intelligence, Jan. 2000, pp. 4-37, vol. 22, No. 1.

Jang, Joung S., et al., The Differential Proteome Profile of Stomach Cancer: Identification of the Biomarker Candidates, Oncol. Res., 2004, pp. 491-499, vol. 14, No. 10.

Jiang, L, et al., Proteomic Analysis of the Cerebrospinal Fluid of Patients with Schizophrenia, Amino Acids, Jul. 2003, pp. 49-57, vol. 25, No. 1.

Kao, L. C., et al., Global Gene Profiling in Human Endometrium During the Window of Implantation, Endocrinology, Jun. 2002, pp. 2119-2138, vol. 143, No. 6.

Karlsson, H., et al., Lipoproteomics I: Mapping of Proteins in Low-Density Lipoprotein Using Two-Dimensional Gel Electrophoresis and Mass Spectrometry, Proteomics, Feb. 2005, pp. 551-565, vol. 5, No. 2.

Karlsson, H., et al., Lipoproteomics II: Mapping of Proteins in High-Density Lipoprotein Using Two-Dimensional Gel Electrophoresis and Mass Spectrometry, Proteomics, Apr. 2005, pp. 1431-1445, vol. 5, No. 5.

Kashyap, M.L., et al., Radioimmunoassay of Human Apolipoprotein CII: A STudy in Normal and Hypertriglyceridemic Subjects, The Journal of Clinical Investigation, Jul. 1977, pp. 171-180, vol. 60.

Kawakami, Takayuki, et al., Proteomic Analysis of Sera from Hepatocellular Carcinoma Patients After Radiofrequency Ablation Treatment, Proteomics, Nov. 2005, pp. 4287-4295, vol. 5, No. 16.

Khovidhunkit, Weerapan, et al., Apolipoproteins A-IV and A-V are Acute-Phase Proteins in Mouse HDL, Atherosclerosis, Sep. 2004, pp. 37-44, vol. 176, No. 1.

Klein, R.L., et al., Apolipoprotein C-III Protein Concentrations and Gene Polymorphisms in Type 1 Diabetes Associations with Microvascular Disease Complications in the DCCT/EDIC Cohort, Journal of Diabetes, 2005, pp. 18-25, vol. 19.

Kuzuya, Akinori, et al., Site-Selective RNA Scission at Two Sites for Precise Genotyping of SNPs by Mass Spectrometry, Chem. Commun. (Camb.), Mar. 21, 2003, pp. 770-771, No. 6.

Kwiterovich, Jr., P.O., A Large High-Density Lipoprotein Enriched in Apolipoprotein C-1: A Novel Biochemical Marker in Infants of Lower Birth Weight and Younger Gestational Age, JAMA, 2005, pp. 1891-1899, vol. 293, No. 15.

Le, N., et al., Lipid and Apolipoprotein Levels and Distribution in Patients With Hypertriglyceridemia: Effect of Triglyceride Reductions with Atorvastatin, Metabolism, Feb. 2000, pp. 167-177, vol. 49, No. 2.

Leak, Lee V., et al., Proteomic Analysis of Lymph, Proteomics, Mar. 2004, pp. 753-765, vol. 4, No. 3.

Lee, Sung-Han, et al., Proteomic Characterization of Rat Liver Exposed to 2,3,7,8-Tetrachlorobenzo-P-Dioxin, J. Proteome Res., Mar.-Apr. 2005, pp. 335-343, vol. 4, No. 2.

Lefler, David M., et al., Identification of Proteins in Slow Continuous Ultrafine by Reversed-phase chromatography and Proteomics, J. Proteome Res., Nov.-Dec. 2004, pp. 1254-1260, vol. 3, No. 6.

Lewczuk, Piotr, et al., Amyloid Beta Peptides in Cerebrospinal Fluid as Profiled with Surface Enhanced Laser Desorption/Ionization Time-of-Flight Mass Spectrometry: Evidence of Novel Biomarkers in Alzheimer's Disease, Biol. Psychiatry, Mar. 1, 2004, pp. 524-530, vol. 55, No. 5.

Little, D.P., et al., Identification of Apoliprotein E Polymorphisms Using Temperature Cycled Primer Oligo Base Extension and Mass Spectrometry, Eur. J. Clin. Chem. Clin. Biochem., Jul. 1997, pp. 545-548, vol. 35, No. 7.

Lund-Katz, S., et al., High Density Lipoprotein Structure, Frontiers in Bioscience, May 1, 2003, pp. d1044-1054, vol. 8.

Macfarlane, R.D., et al., Development of a Lipoprotein Profile Using Capillary Electrophoresis and Mass Spectrometry, Sep. 1997, pp. 1796-1806, vol. 18, No. 10.

Macphee, C.E., et al., Mass Spectrometry to Characterize the Binding of a Peptide to a Lipid Surface, Anal. Biochem., Nov. 1, 1999, pp. 22-29, vol. 275, No. 1.

Malik, et al., Serum Levels of an Isoform of Apolipoprotein A-II as a Potential Marker for Prostate Cancer, Clinical Cancer Research, Feb. 1, 2005, pp. 1073-1085, vol. 11, No. 3.

Mateos-Ceceres, Petra J., et al., Proteomic Analysis of Plasma from Patients During and Acute Coronary Syndrome, J. Am. Coll. Cardiol., Oct. 19, 2004, pp. 1578-1583, vol. 44, No. 8.

Mayr, Manuel, et al., Proteomic and Metabolomic Analyses of Atherosclerotic Vessels from Apolipoprotein E-Deficent Mice Reveal Alterations in Inflammation, Oxidative Stress, and Energy Metabolism, Arterioscler. Thromb. Vasc. Biol., Oct. 2005, pp. 2135-2142, vol. 23, No. 10.

Obici, Laura, et al., Liver Biopsy Discloses a New Apolipoprotein A-I Hereditary Amyloidosis in Several Unrelated Italian Families, Gastroenterology, May 2004, pp. 1416-1422, vol. 126, No. 5.

Ordonez, et al. Apolipoprotein D expression in substantia nigra of Parkinson disease; Histology & Histopathology; 21(4):361-6, Apr. 2006.

Pont, F., et al., Isotope Ratio Mass Spectrometry, Compared with Conventional Mass Spectrometry in Kinectic Studies at Low and High Enrichment Levels: Application to Lipoprotein Kinetics, Anal. Biochem., Jun. 1, 1997, pp. 277-287, vol. 248, No. 2.

Puchades, Maja, et al., Proteomic Studies of Potential Cerebrospinal Fluid Protein Markers for Alzheimer's Disease, Brain Res. Mol. Brain Res., Oct. 21, 2003, pp. 140-146, vol. 118, No. 1-2.

Rezaee, F., et al., Proteomic Analysis of High-Density Lipoprotein, Proteomics, 2006, pp. 721-730, vol. 6.

Rimland, D., et al., Antiretroviral Therapy in HIV-Positive Men is Associated with Increased Apolipoproteins CIII in Triglyceride-Rich Lipoproteins, HIV Medicine, 2005, pp. 326-333.

Rimland, D., et al., Antiretroviral Therapy in HIV-Positive Women is Associated with Increased Apoliproteins and Total Cholestrol, J. Acquir. Immune Defic. Syndr., Jul. 2006, pp. 307-313, vol. 42, No. 3.

Rosenberg, et al., . Apolipoptrotein J/clustering prevents a progressive glomerulopathy of aging; Molecular & Cellular Biology, 22(6):1893-902, Mar. 2002.

Rosenberg, Roger N., Translational Research on the Way to Effective Therapy for Alzheimer Disease, Arch. Gen. Psychiatry, Nov. 2005, pp. 1186-1192, vol. 62, No. 11.

Sakatsume, M., et al., Novel Glomerular Lipoprotein Deposits Associated with Apolipoprotein E2 Homzygosity, Kidney Int., May 2001, pp. 1911-1918, vol. 59, No. 5.

Sasaki, et al., Advanced Glycation End Products in Alzheimer's Disease and Other Neurodegenerative Diseases, American Journal of Pathology, Oct. 1, 1988, pp. 1149-1155, vol. 53, No. 4.

Scheffer, et al., Increased Plasma Apolipoprotein C-III Concentration Independently Predicts Cardiovascular Mortality: The Hoorn Study, Clinical Chemistry, Aug. 2008, pp. 1325-1330, vol. 54, No. 8.

Schweer, H., et al., Determination of Isotopic Ratios of L-Leucine and L-Phenylalanine and Their Stable Isotope Labeled Analogues in Biological Samples by Gas Chromatography/Triple-Stage Quadrupole Mass Spectrometry, J. Mass Spectrom., Jul. 1996, pp. 727-734, vol. 31, No. 7.

Shuvaev, et al., Increased Protein Glycation in Cerebrospinal Fluid of Alzheimer's Disease, Neurobiology of Aging, May-Jun. 2001, pp. 397-402, vol. 22, No. 3.

Sierra-Johnson, et al., ApoB/ApoA-1: An Independent Predictor of Insulin Resistance in US Non-Diabetic Subjects, European Heart Journal, Nov. 2007, pp. 2637-2643, vol. 28, No. 21.

Smith, Richard W., et al., Apolipoprotein AI Could Be a Significant Determinant of Epithelial Integrity in Rainbow Trout Gill Cell Cultures: A Study in Functional Proteomics, Biochim. Biophys. Acta., May 20, 2005, pp. 81-93, vol. 1749, No. 1.

Somiari, Richard I., et al., High-Throughput Proteomic Analysis of Human Infiltrating Ductal Carcinoma of the Breast, Proteomics, Oct. 2003, pp. 1863-1873, vol. 3, No. 10.

Srinivasan, J.R., et al., Genotyping of Apolipoprotein E by Matrix-Assisted Laser Desorption/Ionization Time-of-Flight Mass Spectrometry, Rapid Commun. Mass Spectrom., 1998, pp. 1045-1050, vol. 12, No. 16.

Steel, Laura F., et al., A Strategy for the Comparative Analysis of Serum Proteomes for the Discovery of Biomarkers for Hepatocellular Carcinoma, Proteomics, May 2003, pp. 601-609, vol. 3, No. 5.

Sundsten, T., et al., Serum Protein Patterns in Newly Diagnosed Type 2 Diabetes Mellitus—Influence of Diabetic Environment and Family History of Diabetes, Diabetes/Metabolism Research Reviews, Feb. 2008, pp. 148-154, vol. 24, No. 2.

Tachibana, Masayoshi, et al., Expression of Apolipoprotein A1 in Colonic Adenocarcinoma, Anticancer Res., Sep.-Oct. 2003, pp. 4161-4167, vol. 23, No. 5b.

Tolson, Jonathan, et al., Serum Protein Profiling by SELDI Mass Spectrometry: Detection of Multiple Variants of Serum Amyloid Alpha in Renal Cancer Patients, Lab. Invest., Jul. 2004, pp. 845-856, vol. 84, No. 7.

Tozuka, et al. Annals of Clinical & Laboratory Science, 27(5):351-7, Sep.-Oct. 1997 Characterization of hypertriglyceridemia induced by L-asparaginase therapy for acute lymphoblastic leukemia and malignant lymphoma.

Tysoe, et al., Apo E and Apo C1 Loci are Assocaited with Dementia in Younger But Not Older Late-Onset Cases, Dement Geriatr. Cogn. Disord., 1998, pp. 191-198, vol. 9.

Yamada, m., et al., Identification of Low-Abundance Proteins of Bovine Colostral and Mature Milk Using Two-Dimensioinal Electrophoresis Followed by Microsequencing and Mass Spectrometry, Electrophoresis, Apr. 2002, pp. 1153-1160, vol. 23, No. 7-8.

Yang, Jae-Won, et al., Extravasation of Plasma Proteins Can Confound Interpretation of Proteomic Studies of Brain: A Lesson from APO A-I in Mesial Temporal Lobe Epilepsy, Brain Res. Mol. Brain, Res., Oct. 3, 2005, pp. 348-356, vol. 139, No. 2.

Ying-Tao, Zhang, et al., Proteomic Analysis of Differentially Expressed Proteins Between Metastatic and Non-Metastatic Human Colorectal Carcinoma Cell Lines, Eur. J. Gastroenterol Hepatol, Jul. 2005, pp. 725-732, vol. 17, No. 7.

Yocum, Anastasia K., et al., Effect of Immunoaffinity Depletion of Human Serum During Proteomic Investigations, J. Proteome Res., Sep.-Oct. 2005, pp. 1722-1731, vol. 4, No. 5.

Yu, Kenneth H., et al., Characterization of Proteins in Human Pancreatic Cancer Serum Using Differential In-Gel Electrophoresis and Tandem Mass Spectrometry, J. Proteome Res., Sep.-Oct. 2005, pp. 1742-1751, vol. 4, No. 5.

Zhang, Zhen, et al., Three Biomarkers Identified from Serum Proteomic Analysis for the Detection of Early Stage Ovarian Cancer, Cancer Res., Aug. 15, 2004, pp. 5882-5890, vol. 64, No. 16.

Alaupovic, P., et al., Profiles of Apolipoproteins and Apolipoprotein B-Containing Lipoprotein Particles in Dyslipoproteinemias, Clin. Chem., 1988, pp. B13-B27, vol. 34, No. 8B.

Alborn, et al. Relationship of apolipoprotein A5 and apolipoprotein C3 levels to serum triglycerides in patients with type 2 diabetes; Clinica Chimica Acta, 378(1-2):154-8, Mar. 2007.

Alexander, Hannah, et al., Proteomic Analysis to Identify Breast Cancer Biomarkers in Nipple Aspirate Fluid (Abstract), Clin. Cancer Res., Nov. 15, 2004, pp. 7500-7510, vol. 10, No. 22.

Alfonso, P., et al., Identification of Cellular Proteins Modified in Response to African Swine Fever Virus Infection by Proteomics, Proteomics, Jul. 2004, pp. 2037-2046, vol. 4, No. 7.

Allard, et al., ApoC-1 and ApoC-III as Potential Plasmatic Markers to Distinguish Between Ischemic and hemorrhagic stroke, Proteomics, Aug. 2004, pp. 2242-2251, vol. 4, No. 8.

Avogaro, P., et al., Are Apolipoproteins Better Discriminators Than Lipids for Atherosclerosis?, The Lancet, Apr. 28, 1979, pp. 901-903.

Bard, Jean-Marie, et al., Association of Apolipoproteins C3 and E with Metabolic Changes in HIV-Infected Adults Treated with a Protease-Inhibitor-Containing Antiretroviral Therapy, Antiviral Therapy, pp. 361-370, vol. 11, 2006.

* cited by examiner

FIGURE 1A

TABLE 1. Calculated and measured molecular weight of apoC-III (daltons)

|  | | Measured $M_r^b$ | |
| --- | --- | --- | --- |
| Calculated $M_r^a$ | Subject 1 | Subject 2 | Subject 3 |
| ApoC-III$_0$ 8764.2 | 8763.9(−0.3) | 8764.9(±0.7) | 8765.5(+1.3) |
| ApoC-III$_1$ 9420.8 | 9420.6(−0.2) | 9420.0(−0.8) | 9422.2(+1.4) |
| ApoC-III$_3$ 9712.1 | ≥9700.2(−11.9) | | |

Ito Y, Breslow JL, Chait BT. Apolipoprotein C-IIIO lacks carbohydrate residues: use of mass spectrometry to study apolipoprotein structure. J Lipid Res. 1989 Nov; 30(11):1781-7.

Ito Y, Breslow JL, Chait BT. Apolipoprotein C-IIIO lacks carbohydrate residues: use of mass spectrometry to study apolipoprotein structure. J Lipid Res. 1989 Nov; 30(11):1781-7.

FIGURE 5
Apolipoprotein CIII Isoforms Reproducibility Ciphergen Anti-CIII PS 20 Chip
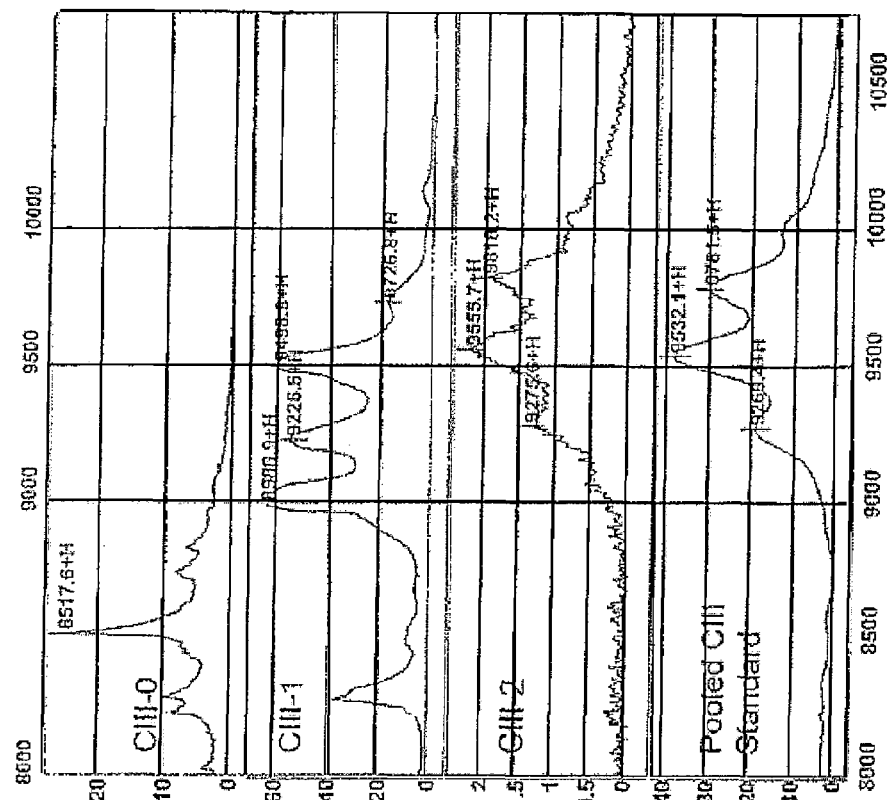
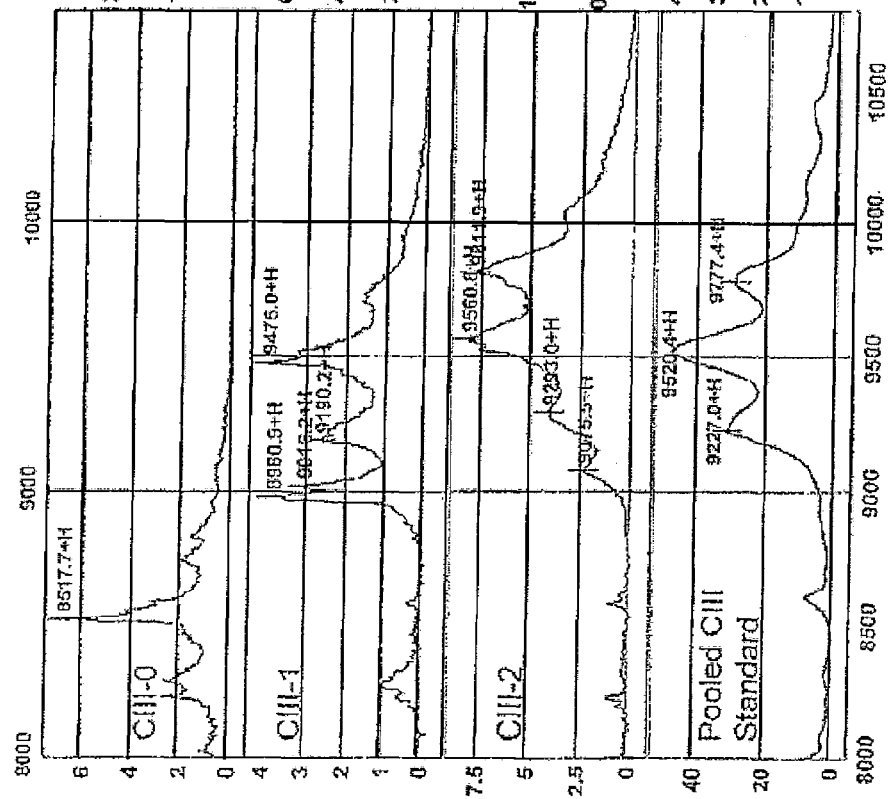

FIGURE 8

Plasma CIII Isoform Profile at Different Plasma Dilutions

| Trial | CIII-0 pk1 | CIII-0 pk2 | CIII-0 pk3 | CIII-0 pk4 | CIII-1 | CIII-2 |
|---|---|---|---|---|---|---|
| Chip1 | 8780.7 | 8826.3 | 8931.1 | 9146.3 | 9436.4 | 9726.1 |
| Chip2 | 8780.6 | 8826.3 | 8931.3 | 9147.7 | 9435.9 | 9725.8 |
| Chip3 | 8779.7 | 8825.1 | 8929.7 | 9145.3 | 9434.8 | 9724.9 |
| Chip4 | 8778.8 | 8823.9 | 8928.7 | 9145.2 | 9433.4 | 9723.0 |
| Average | 8780.0 | 8825.4 | 8930.2 | 9146.1 | 9435.1 | 9725.0 |
| Std Dev | 0.889 | 1.149 | 1.227 | 1.162 | 1.330 | 1.396 |
| Expected | 8764.4 | | | | 9420 | 97112 |

Comparison of Apolipoprotein CIII Isoforms Profile of Normal and Diabetic Subjects Ciphergen Anti-CIII PS 20 Chips Direct Plasma Tests for
Cardiovascular Disease and Related Disorders

APOLIPOPROTEIN FINGERPRINTING TECHNIQUE AND METHODS RELATED THERETO

CROSS-REFERENCE AND PRIORITY CLAIM

The present U.S. Non-Provisional Patent Application, is a continuation-in-part of Patent Cooperation Treaty Application no. PCT/US2007/007359, publication no. WO 2007/112005 A2, entitled "Apolipoprotein Fingerprinting Technique," filed on Mar. 23, 2007, on behalf of inventors Emelita De Guzman Breyer and Mary K. Robinson, which claims priority to and the benefit of U.S. Provisional patent application entitled "APOLIPOPROTEIN FINGERPRINTING TECHNIQUE filed Mar. 23, 2006, on behalf of inventors Emelita De Guzman Breyer and Mary K. Robinson, having Ser. No. 60/743,678.

COPYRIGHT NOTICE

A portion of the disclosure of this patent document may contain material which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

BACKGROUND

I. Field of the Invention

The present invention relates to the field of compositions, analysis and quantification of apolipoproteins in biological and clinical samples. More particularly, this invention relates to methods, techniques, and protocols for the fingerprinting, profiling, determining, and/or quantifying of apolipoproteins present in samples of human biological matrices, such as, for example and without limitation, plasma, urine, serum and lipoprotein fractions.

II. Description of the Related Art

It is well accepted that apolipoproteins, the protein components of lipoproteins, are able to solubilize hydrophobic lipids and facilitate cell targeting and transport. These components, synthesized in the liver and intestine, are essential for maintaining the integrity of lipoprotein particles, serving as cofactors for enzymes that act on lipoproteins, and facilitating receptor-mediated interactions that remove lipids from circulation.

There are several groups of apolipoproteins: A (Apo A), B (Apo B), C (Apo C) and E (Apo E). Each of the three groups A, B and C consists of two or more distinct proteins. These are Apo A1, Apo A11, Apo AIV, and AV for Apo A; Apo B100 and Apo B48 for Apo B; and Apo CI, Apo Cli, Apo CIII, and Apo CIV for Apo C. Apo CI, CIII, CIV and Apo E each consist of two or more isoforms. The apolipoproteins have various roles in disease and in health.

Apolipoprotein CIII is a 79 amino acid protein that exists in humans as three isoforms differing in the glycosylation at Threonine-74. CIII-0 isoform is the final product of sialidase enzyme reactions, has an absence of sialic acid, galactose and galactose amine residues, and accounts for 14% of the total isoforms. CIII-0 isoforms are inhibitors of very low density lipoproteins (VLDL) binding to the lipolysis stimulated receptor, which is an important route of clearance of high triglyceride lipoproteins in plasma. CIII-0 isoform has the lowest affinity to VLDL. CIII-1 isoform has 1 mole of sialic and counts for 51% of total isoforms. CIII-2 isoform is the initial form of CIII synthesized and secreted in the liver, has 2 mole of sialic acid, and accounts for 35% of total isoforms. CIII-2 isoform has a higher affinity to VLDL and is a poorer inhibitor of VLDL binding to the lipolysis stimulated receptor.

Current methods to identify and quantitate CIII isoforms involve isolation of lipoprotein fractions from plasma, delipidation of this fraction, and purification of the CIII from the water-soluble fraction of apolipoproteins. Although the different purified isoforms can all be detected by isoelectric focusing gel electrophoresis, mass spectrometry, and fluorescence and absorbance spectroscopy, no individualization, differentiation, or relative quantification of a mixture of isoforms is provided by or within such results. Separation of the isoforms must be accomplished first, such as by ion exchange chromatography, if specific detection information regarding a particular isoform is desired. That is, current methods are disadvantageous in that they are tedious in isolation of CIII from plasma, having only a 60-80% protein recovery, and in that current methods for clinical diagnostics for CIII in plasma, such as ELISA and immunoturbidimetric assays, only can detect total CIII.

However, CIII isoforms are clinically significant for several reasons. The levels of the isoforms change with the level of glucose control in diabetic patients.[1] For example, high HbA1C directly correlates to high CIII-0 levels.[2] Hypertriglyceridemic subjects have an increased proportion of CIII as the CIII-2 isoform in VLDL. CIII-2 levels increase in females subjected to severe caloric restriction despite normal total CIII levels. The variation in CIII-2 positively correlates to changes in VLDL triglycerides while the variation of CIII-1 inversely correlates. Because of the limitations in the existing techniques with respect to the accurate quantitation and detection of the CIII isoforms, the role of these isoforms in various metabolic processes, although of great importance in understanding lipid metabolism, is still subject to controversy.

[1]Sundsten, T., Ostenson, Claes-Goran, Bergsten, P., *Diabetes/Metabolism Research Reviews,* 24(2):148-54, 2008 February, Serum Protein Patterns in Newly Diagnosed Type 2 Diabetes Mellitus—Influence of Diabetic Environment and Family History of Diabetes.
[2]Florez, H., Mendez, A., Casanova-Romero, P., Larreal-Urdaneta, C., Castillo-Florez, S., Lee, D., and Goldberg, Ronald., *Atherosclerosis,* 188(1):134-41, 2006, September, Increased Apolipoprotein C-III Levels Associated with Insulin Resistance Contributed to Dyslipidemia in Normoglycemic and Diabetic subjects from a Triethnic Population.

The literature or prior art report various characterizations and correlations between various apolipoproteins and diseases. For example, Apo D is a multi-ligand, multifunctional transporter and is known to accumulate in a specific site of regenerating peripheral nerves in Alzheimer's disease.[3] Further, Apo J so far has been reportedly implicated in several diverse physiological processes, such as sperm maturation, lipid transportation, complement inhibition, tissue remodeling, membrane recycling, cell-cell and cell-substratum interactions, stabilization of stressed proteins in a folding-competent state, and promotion or inhibition of apoptosis. Also, Apo H is known to bind tightly to negatively charged surfaces and to inhibit the activation of the intrinsic pathway of blood coagulation and the prothrombinase activity of activated platelets by covering the negatively charged surfaces necessary for both activities. Apo F associates with LDL and inhibits cholesterol ester transfer protein (CETP) activity, and appears to be an important regulator of cholesterol transport. Apo F associates to a lesser degree with VLDL, Apo A1 and Apo A11. Apo M was proposed to be involved in lipid transport.[4] Apo CIV is a 14.5 kD size apolipoprotein in the same locus as CI and CII, yet no function appears to be reported in the literature.

[3] Shuvaev, et al., *Neurobiology of Aging*, 22(3):397-402, 2001 May-June. Increased protein glycation in cerebrospinal fluid of Alzheimer's disease; Christen, Y. *American Journal of Clinical Nutrition*, 71(2):621S-629S, 2000 February. Oxidative stress and Alzheimer disease; Sasaki, et al., *American Journal of Pathology*, 153(4):1149-55, 1988 October. Advanced glycation end products in Alzheimer's disease and other neurodegenerative diseases.

[4] Feingold, et al., *Atherosclerosis*, 199(1):19-26, 2008 July. Infection and inflammation decrease apolipoprotein M expression; Huang, et al. *Medical Hypotheses*, 69(1):136-40, 2007. Apolipoprotein M likely extends its anti-atherogenesis via anti-inflammation; Dahlback, et al. *Current Opinion in Lipidology*, 17(3):291-5, 2006 Jun. Apolipoprotein M—a novel player in high-density lipoprotein metabolism and atherosclerosis.

Further, based on epidemiological correlation between cardiovascular disease and cholesterol levels, clinicians have long measured and standardized the measurement of cholesterol levels to assess risks of heart disease. Lipoprotein particles (LDL and HDL) and the cholesterol associated with them also have been used in the assessment of cardiovascular risks.[5] Many research studies have been conducted to relate health effects to lipoprotein particle sizes and densities, but the conclusions from these studies have not been consistent.

[5] Chen, et al., *International Journal of Urology*, 12(10):886-91,2005 October. Antiandrogenic therapy can cause coronary arterial disease; Florez, et a., *Atherosclerosis*, 188(1):134-41, 2006, September, Increased Apolipoprotein C-III Levels Associated with Insulin Resistance Contribute to Dyslipidemia in Normoglycemic and Diabetic subjects from a Triethnic Population; Scheffer, et al. *Clinical Chemistry* 54(8):1325-30, 2008 August. Increased plasma apolipoprotein C-III concentration independently predicts cardiovascular mortality: the Hoorn Study; Gervaise, et al. *Diabetologia*, 43(6):703-8, 2000 June. Triglycerides, apo C3 and Lp B:C3 and cardiovascular risk in type II diabetes; Huang, et al. *Medical Hypotheses*, 69(1): 136-40, 2007. Apolipoprotein M likely extends its anti-atherogenesis via anti-inflammation; Dahlback, et al. *Current Opinion in Lipidology*, 17(3):291-5, 2006 June. Apolipoprotein M-a novel player in high-density lipoprotein metabolism and atherosclerosis.

Over the last few years, there has been considerable evidence that apolipoprotein levels are associated with a variety of conditions, and recently the National Heart, Lung, and Blood Institute (NHLBI), in a recent meeting with the Centers for Disease Control and Prevention, recommended that apolipoprotein B measurements be included for standardization in the near future. Apolipoproteins have been associated with cardiovascular disease, diabetes, stroke, obesity, Alzheimer's, HIV, and other diseases.[6] Given the primary role of apolipoproteins in the transport and metabolism of lipids, these associations are not surprising. The difficulty of purifying, detecting, and quantifying apolipoproteins, however, has not made it easy to conduct investigations between levels of these compounds and health effects.

[6] Allard, et al. *Proteomics.* 4(8):2242-51,2004 August. ApoC-1 and ApoC-III as potential plasmatic markers to distinguish between ischemic and hemorrhagic stroke; Sierra-Johnson, et al., *European Heart Journal*, 28(21):2637-43, 2007 November. ApoB/apoA-1: an independent predictor of insulin resistance in US non-diabetic subjects; Florez, et al., *Atherosclerosis*, 188(1):134-41, 2006 September. Increased apolipoprotein C-III levels associated with insulin resistance contribute to dyslipidemia in normoglycemic and diabetic subjects from a triethnic population; Malik, et al. *Clinical Cancer Research*, 11(3):1073-85, 2005 Feb. 1. Serum levels of an isoform of apolipoprotein A-II as a potential marker for prostate cancer; Chen, et al., *International Journal of Urology*, 12(10):886-91, 2005 October. Antiandrogenic therapy can cause coronary arterial disease; Sundsten, et al., *Diabetes/Metabolism Research Reviews*, 24(2):148-54, 2008 February. Serum protein patterns in newly diagnosed type 2 diabetes mellitus-influence of diabetic environment and family history of diabetes; Alborn, et al. *Clinica Chimica Acta*, 378(1-2):154-8, 2007 Mar. Relationship of apolipoprotein A5 and apolipoprotein C3 levels to serum triglycerides in patients with type 2 diabetes; Florez, et a, *Atherosclerosis*, 188(1):134-41, 2006, September, Increased Apolipoprotein C-Ill Levels Associated with Insulin Resistance Contribute to Dyslipidemia in Normoglycemic and Diabetic subjects from a Triethnic Population; Dallinga-Thie, et al. *Diabetoloia* 49(7):1505-11, 2006 July. Plasma apolipoprotein A5 and triglycerides in type 2 diabetes; Davidsson, et al., *Journal of Lipid Research*, 46(9):1999-2006, 2005 September. A proteomic study of the apolipoproteins in LDL subclasses in patients with the metabolic syndrome and type 2 diabetes; Rimland, et al., *Journal of Acquired Immune Deficiency Syndromes*: JAIDS, 42(3):307-13, 2006 July. Antiretroviral therapy in HIV-positive women is associated with increased apolipoproteins and total cholesterol; Feingold, et al., *Atherosclerosis*, 199(1):19-26, 2008 July Infection and inflammation decrease apolipoprotein M expression; Shuvaev, et al., *Neurobiology of Aging*, 22(3):397-402, 2001 May-June. Increased protein glycation in cerebrospinal fluid of Alzheimer's disease; Christen, Y. *American Journal of Clinical Nutrition*, 71(2):621S-629S, 2000 February. Oxidative stress and Alzheimer disease; Sasaki, et al., *American Journal of Pathology* 153(4):1149-55, 1988 October. Advanced glycation end products in Alzheimer's disease and other neurodegenerative diseases; Rosenberg, et al., *Molecular & Cellular Biology*, 22(6):1893-902, 2002 March. Apolipoptrotein J/clustering prevents a progressive glomerulopathy of aging; Scheffer, et al. *Clinical Chemistry*, 54(8): 1325-30, 2008 August Increased plasma apolipoprotein C-III concentration independently predicts cardiovascular mortality: the Hoorn Study; Gervaise, et al. *Diabetologia*, 43(6):703-8, 2000 June Triglycerides, apo C3 and Lp B:C3 and cardiovascular risk in type II diabetes; Ordonez, et al. *Histology & Histopathology*, 21(4):361-6, 2006 April Apolipoprotein D expression in substantia nigra of Parkinson disease; Tozuka, et al. *Annals of Clinical & Laboratory Science*, 27(5):351-7, 1997 September-October Characterization of hypertriglyceridemia induced by L-asparaginase therapy for acute lymphoblastic leukemia and malignant lymphoma; Favrot, et al. *Biomedicine & Pharmacotherapy*, 38(1):55-9, 1984. Study of blood lipids in 30 children with malignant hematological disease or carcinoma; Huang, et al. *Medical Hypotheses*, 69(1): 136-40, 2007. Apolipoprotein M likely extends its anti-atherogenesis via anti-inflammation; Dahlback, et al. *Current Opinion in Lipidology*, 17(3):291-5, 2006 June Apolipoprotein M-a novel player in high-density lipoprotein metabolism and atherosclerosis.

Using prior art methodology, the quantification and measurement of apolipoprotein currently requires the step of separation of lipoprotein particles from serum by analytical or sequential ultracentrifugation, column chromatography, electrophoresis, or precipitation. These traditional techniques currently are too expensive and time consuming for routine clinical use. Another useful technique is high performance liquid chromatography, which is faster but much more complex and expensive. Other techniques presently used for measurement of Apo A and B content include enzyme immunoassay (ELISA), radioimmunoassay, fluorescence immunoassay, radial immunodiffusion, nephelometry, turbidimetry and electroimmunoassay. Recently, surface-enhanced laser desorption ionization mass spectrometry (SELDI or SELDITOF-MS, with TOF meaning time of flight and MS meaning mass spectrometry) has offered some new options for measuring apolipoproteins in plasma, serum, and lipoprotein fractions. However, each known technique is disadvantageous at least in that a single apolipoprotein must be targeted for quantification and measurement, thus requiring a plurality of lengthy, complex, and expensive techniques to be performed if information regarding a plurality of apolipoproteins is desired. Further, profiles of total plasma or serum require elaborate clustering and pattern recognition techniques to detect differences in samples of normal and healthy individuals.

Accordingly, there is always a need for accurate, rapid, reproducible assays for the separation, identification, and quantification of apolipoproteins. There is a need for improved techniques for the fingerprinting, profiling, determining, and/or quantifying of apolipoproteins present in biological matrices, such as samples of human plasma, serum and lipoprotein fractions, urine, or the like, whereby the phenotype of a particular individual human may be characterized in lieu of or in addition to the genotype. It is to these needs among others that the present invention is directed.

BRIEF SUMMARY OF THIS INVENTION

Briefly, the technique of this invention combines immunological techniques with surface enhanced laser desorption/ionization, SELDI, to facilitate detection and measurement of multiple apolipoproteins directly in biological matrices, such as, for exemplary purposes only, urine, unfractionated plasma or serum, or in lipoprotein fractions, or any other suitable biological matrix. Moreover, internal standards facilitate enhanced confidence of results, wherein detection and measurement of known proteins having very similar antibody-binding properties to the proteins of interest, but with a visibly different molecular mass, may be co-analyzed in order that the mass of the unknown polypeptide(s) determined by mass spectrometry may be compared to the mass of the internal standard reference polypeptide of known identity and concentration. In such manner, previously unrecognized systemic limitations may be essentially overcome.

According to its major aspects, and briefly stated, the preferred apolipofingerprinting technique, as described herein, enables separation, concentration, and detection of one or more apolipoproteins on one surface, rather than requiring, for example, extraction and delipidation of the sample, and then a selection of either a charged chip or a series of chips, according to the apolipoprotein for which information being sought.

As noted above, according to known methodologies, profiles of total plasma or serum require elaborate clustering and pattern recognition techniques to detect differences in samples of normal and healthy individuals. The use of specific antibodies in SELDI technology, however, leads to a much simpler method of analysis. Another simplifying feature of the SELDI technology is retentate chromatography. Proteins of interest are retained by their binding to a specific surface while other analytes are washed away, wherein absorption and desorption can be modified by adjustments in pH, salt concentration or organic solvents. Sinapinic acid or another appropriate matrix is mixed in a freshly prepared solution with tetrafluoroacetic acid and applied to the so-called chip and, upon drying, the matrix-embedded analyte molecules are desorbed by a laser, ionized from the solid phase, and accelerated as intact molecular ions. These SELDI features are further exploited by the improved technique of the present invention.

One embodiment of the preferred technique of the present invention uses specific antibodies, bound to surface-enhanced chips via Protein G, or similarly functional antibody capture protein or molecule, to selectively absorb apolipoproteins directly from plasma samples. The preferred Protein G binds the fc portion of the selected antibodies, resulting in an intentional directional positioning thereof that serves to reproducibly enhance the binding of the antibodies to specific antigens of interest in biological samples. One or more of the specifically targeted apolipoproteins in a biological sample are thus retained on the surface of the surface-enhanced chips, while other sample components are washed away. The EAM (energy absorbing molecule) solution matrix facilitates laser desorption ionization of the apolipoproteins. The ionized apolipoproteins reach the detector at slightly different times based on their times of flight, which time differences can be converted to masses. The intensities of the peaks are related to the quantity of each protein. Thus, total apolipoprotein, as well as isoforms, may be identified and quantitated, resulting in the efficient development of an apolipoprotein profile for a target sample from a singular technique. Moreover, the technique provides for a beneficial increase in quality control by enabling the inclusion of internal standards, thus increasing quality assurance, accuracy and reproducibility of the results.

The compositions, levels, and isoforms of apolipoproteins in biological matrices, plasma and in lipoprotein fractions are determinant of several disorders or conditions related to cardiovascular disease and other chronic disorders such as stroke, metabolic syndrome, inflammation, Parkinson's disease, diabetes, Alzheimer's, HIV and HIV patients under protease inhibitors (hypertriglyceridemic), and various types of lipoproteinemia.[7] For example, a clinical diagnostic assay for CIII isoforms, according to the presently described technique, could beneficially indicate potential disorders, including, but not limited to, those mentioned above. Clinical studies using lipid-lowering drugs would benefit from the apolipoprotein fingerprinting techniques of the present invention, wherein the techniques of the present invention would enable a valuable look at the levels and distribution of apolipoproteins and their isoforms in biological matrices, such as plasma and in different lipoprotein fractions to show how these parameters change with different disorders and treatments. The techniques of the present invention also are ideal for assessing apolipoprotein status in newborns and for evaluating apolipoprotein modifications that occur with aging, nutrition, environmental exposures, and lifestyle changes.
[7]Id.

Illustrative applications of the presently described technique include defining disease specific apolipoprotein biomarkers or profiles and developing quantitative assays that are rapid and useful for diagnosis or categorizing one or more diseases or conditions. These features, and other features and advantages of the present invention will become more apparent to those of ordinary skill in the relevant art when the following detailed description of the preferred embodiments is read in conjunction with the appended drawings.

BRIEF DESCRIPTION OF THE FIGURES

The present invention will be better understood by reading the Detailed Description of the Preferred and Alternate Embodiments with reference to the accompanying drawing figures, which illustrate representative isoform standards and profile reproducibility for the invention, in which like reference numerals denote similar structure and refer to like elements throughout, and in which:

FIG. 1A is a table of Molecular Weights of the Different CIII Isoform Standards;

FIG. 5 is a representation of CIII Isoforms Profile Reproducibility CIPHERGEN Anti-CIII PS 20 chip;

FIG. 8 is a representation of Plasma CIII Isoform Profile at Different Plasma Dilutions;

DETAILED DESCRIPTION OF THE PREFERRED EMBODIMENTS

Figure 1B:
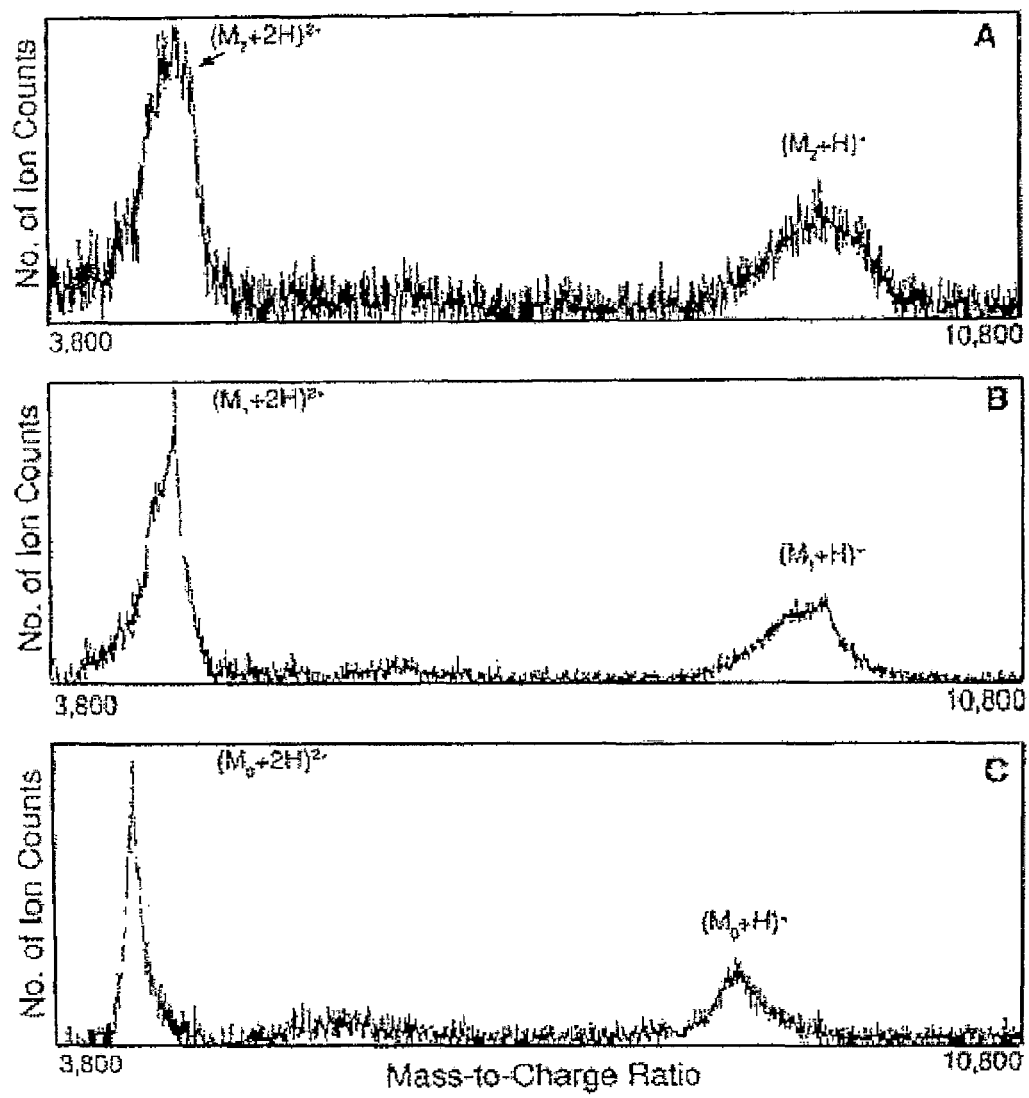
FIG. 1B is a representation of Reported Mass Spectra and Molecular Weights of the Different CIII Isoform Standards.
Figure 2:
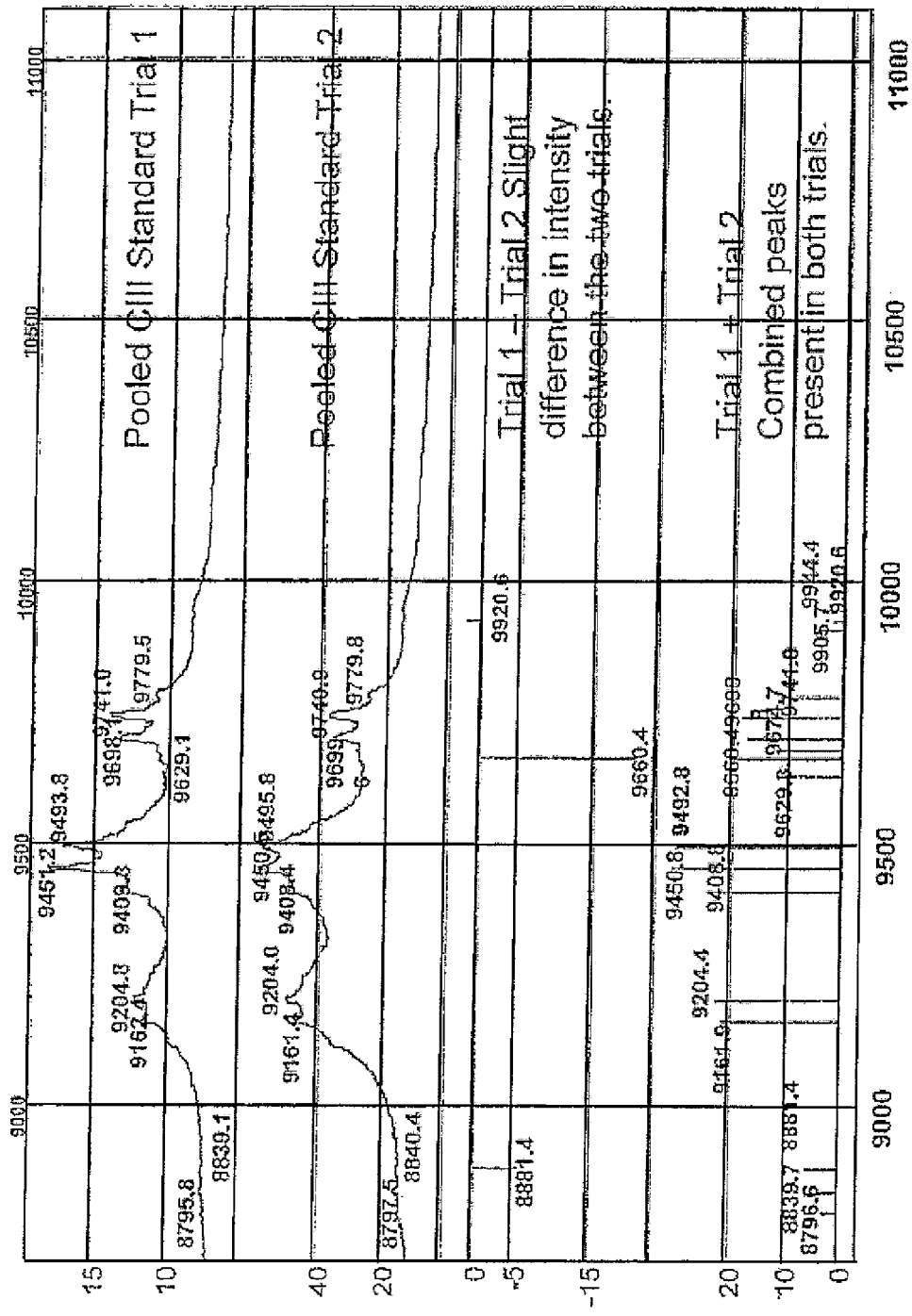
FIG. 2 is a representation of Pooled Apolipoprotein CIII (CIII-0, CIII-1, and CIII-2 Isoforms) Profile CIPHERGEN Q10 chip.
Figure 3:
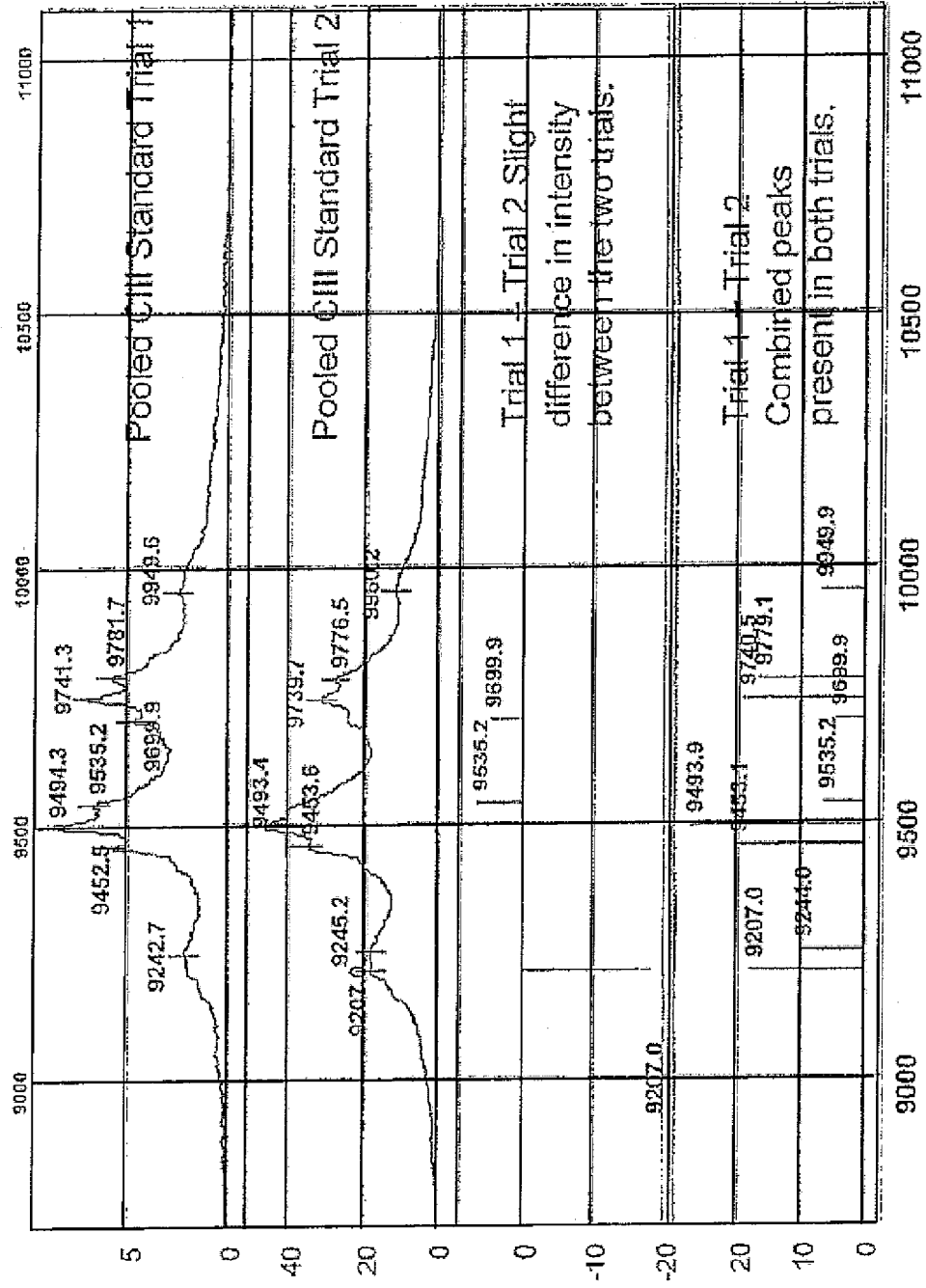
FIG. 3 is a representation of Pooled Apolipoprotein CIII (CIII-0, CIII-1, and CIII-2 Isoforms) Profile CIPHERGEN CM10 chip.
Figure 4A:
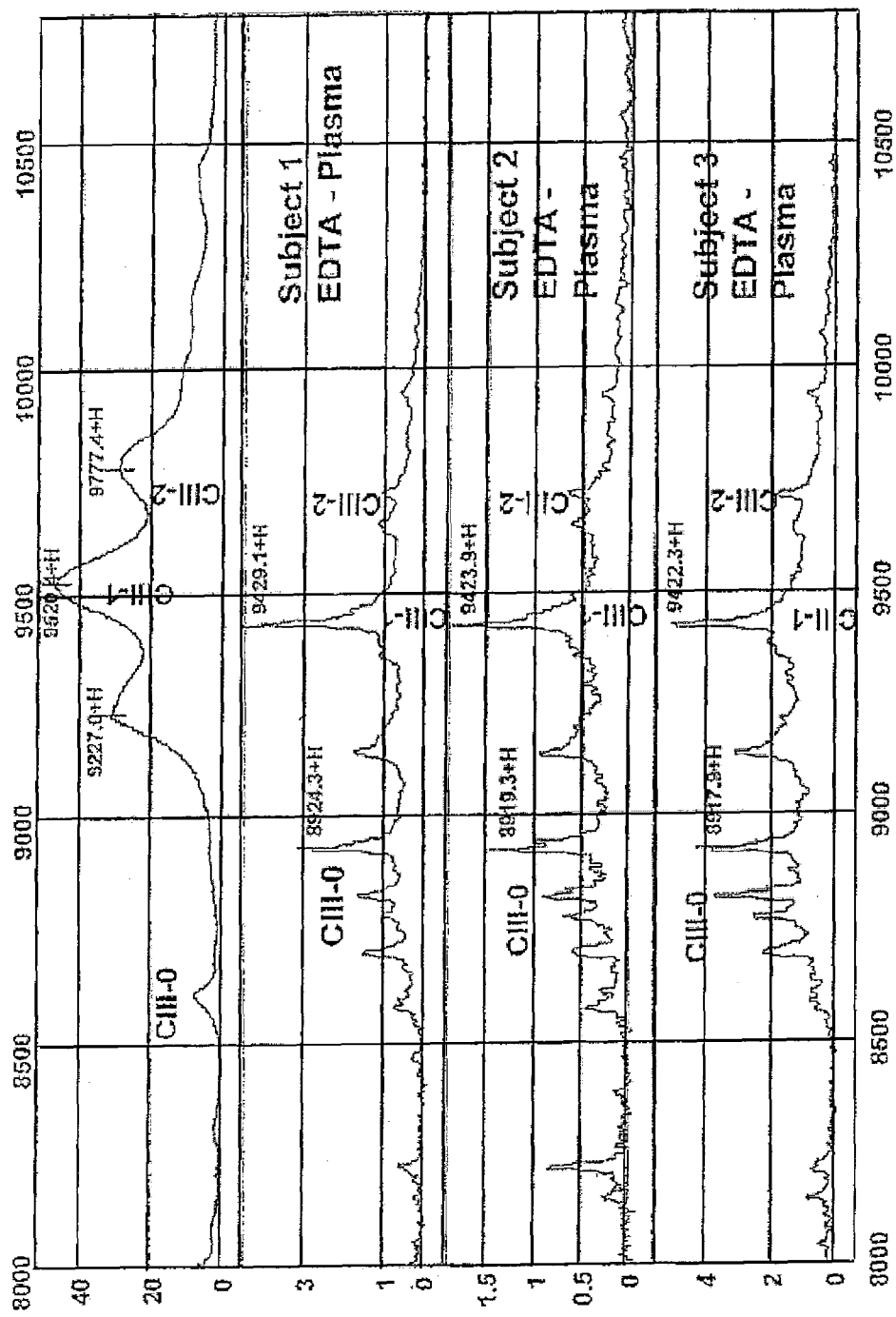
FIG. 4A is a first representation of CIII Isoforms Profile Reproducibility CIPHERGEN Anti-CIII PS 20 chip.
Figure 4B:
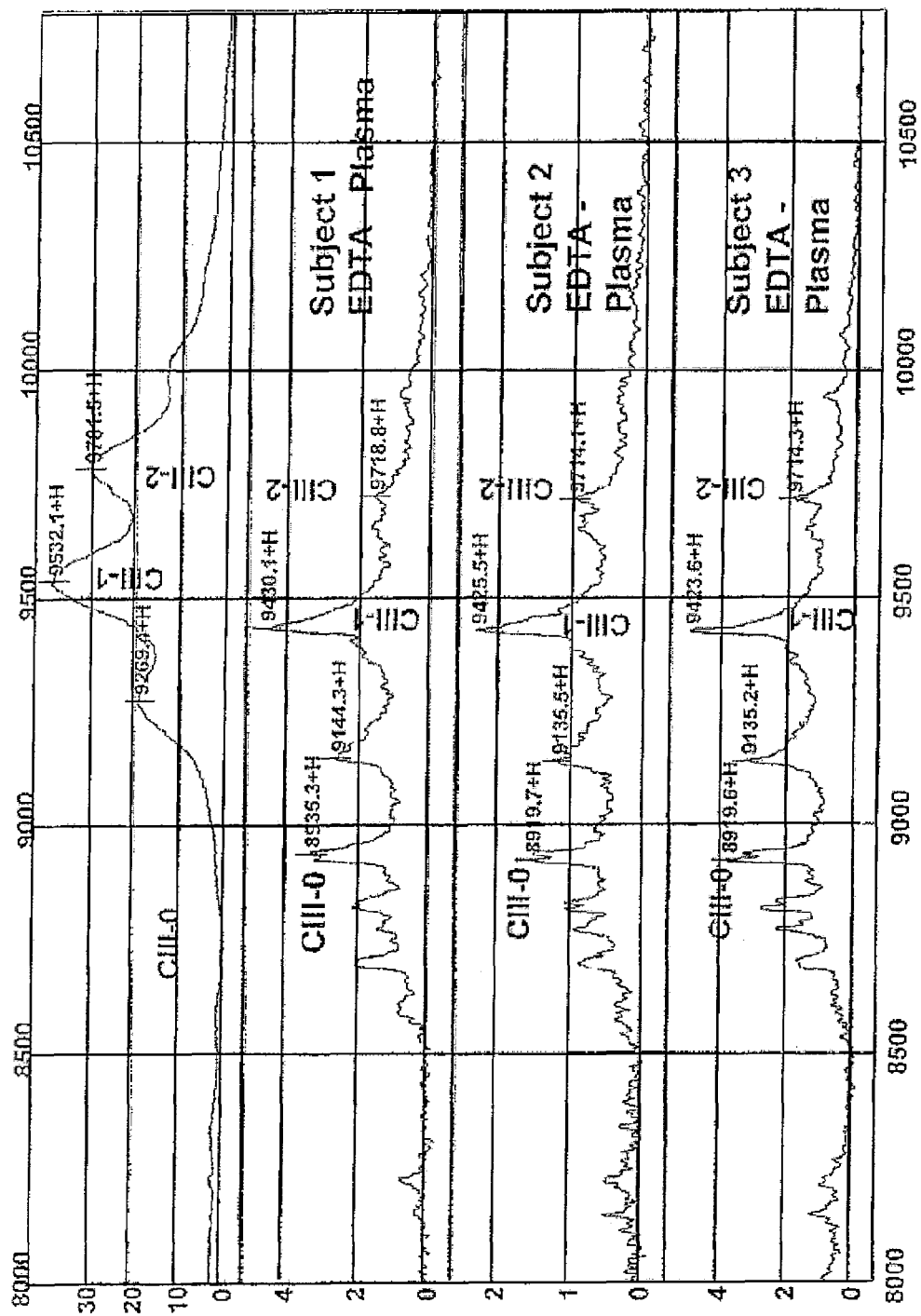
FIG. 4B is a second representation of CIII Isoforms Profile Reproducibility CIPHERGEN Anti-CIII PS 20 chip.
Figure 6:
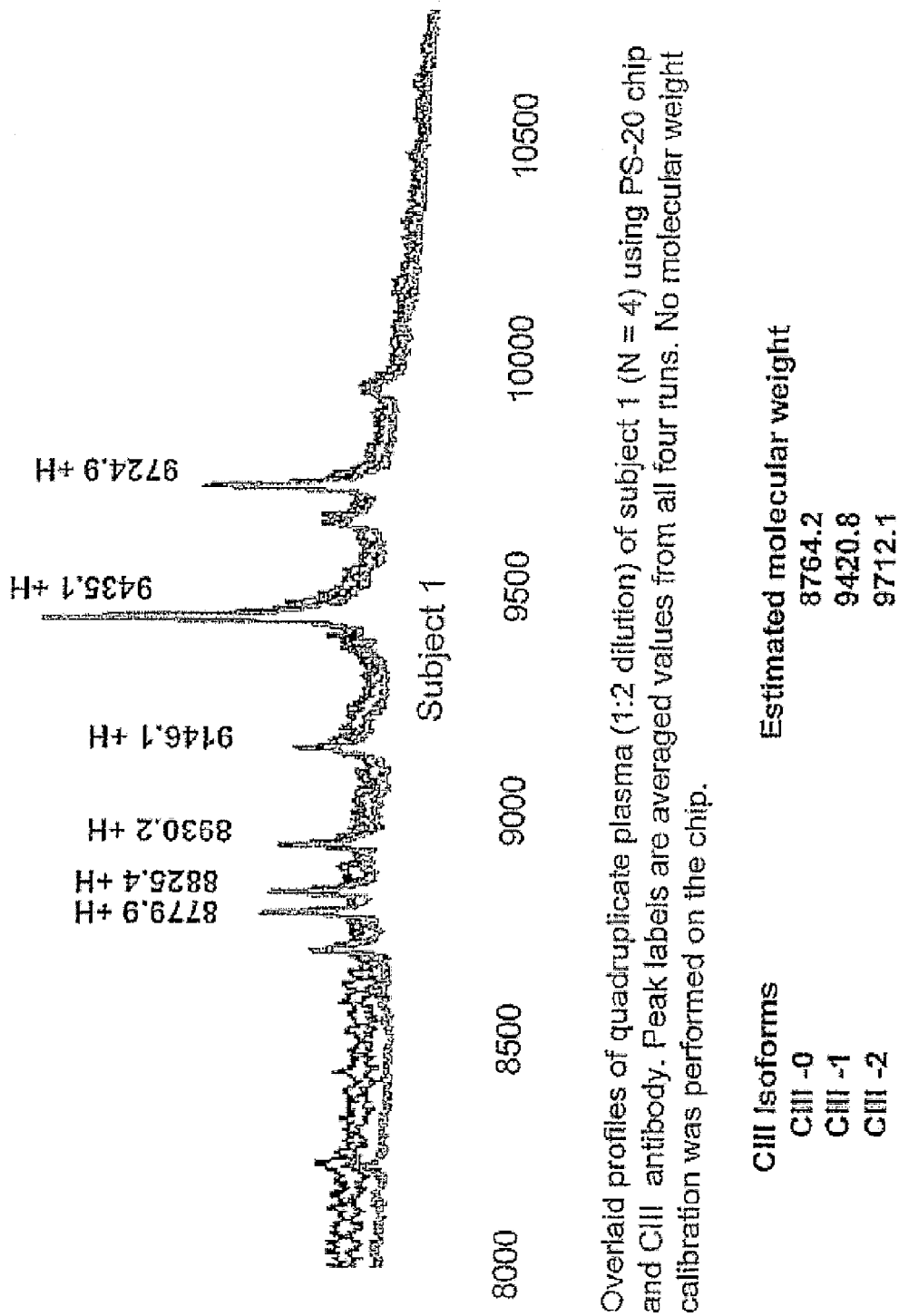
FIG. 6 is a representation of Plasma CIII Isoform Profile Reproducibility.
Figure 7:
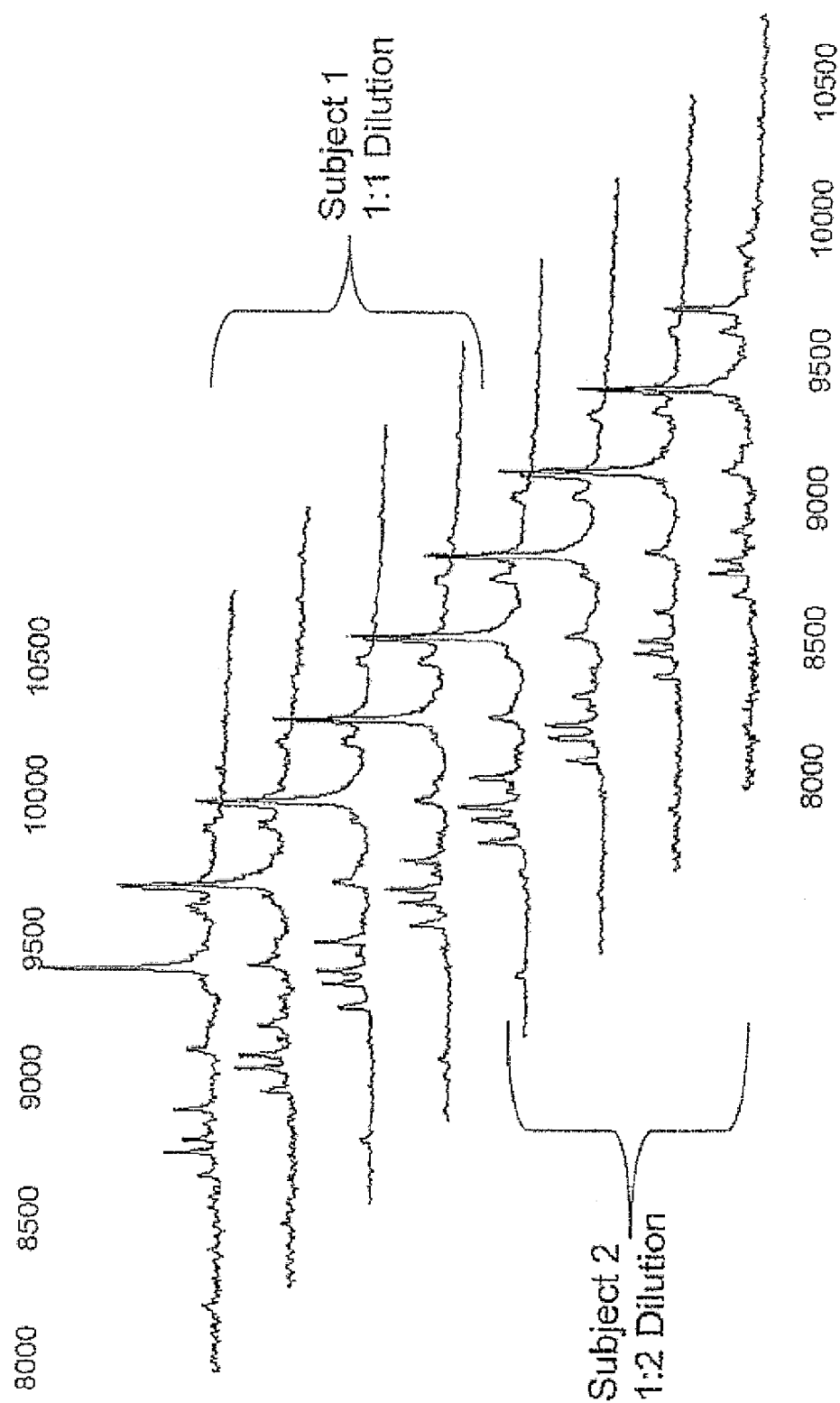
FIG. 7 is a representation of Plasma CIII Isoform Profile at Different Plasma Dilutions.
Figure 9:
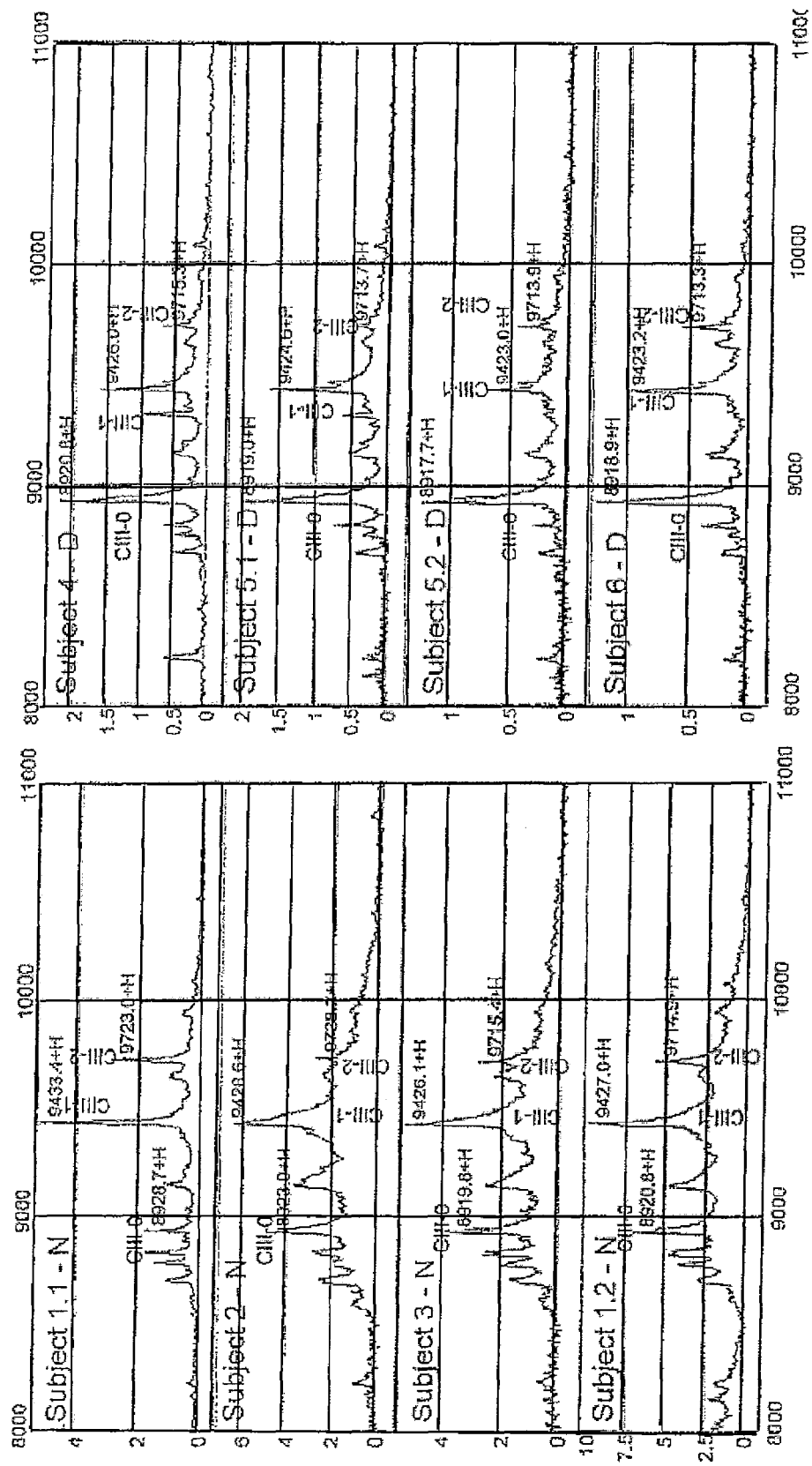
FIG. 9 is a representation of Comparison of CIII Isoform Profile of Normal and Diabetic Subjects CIPHERGEN Anti-CIII PS 20 chip.
Figure 10:
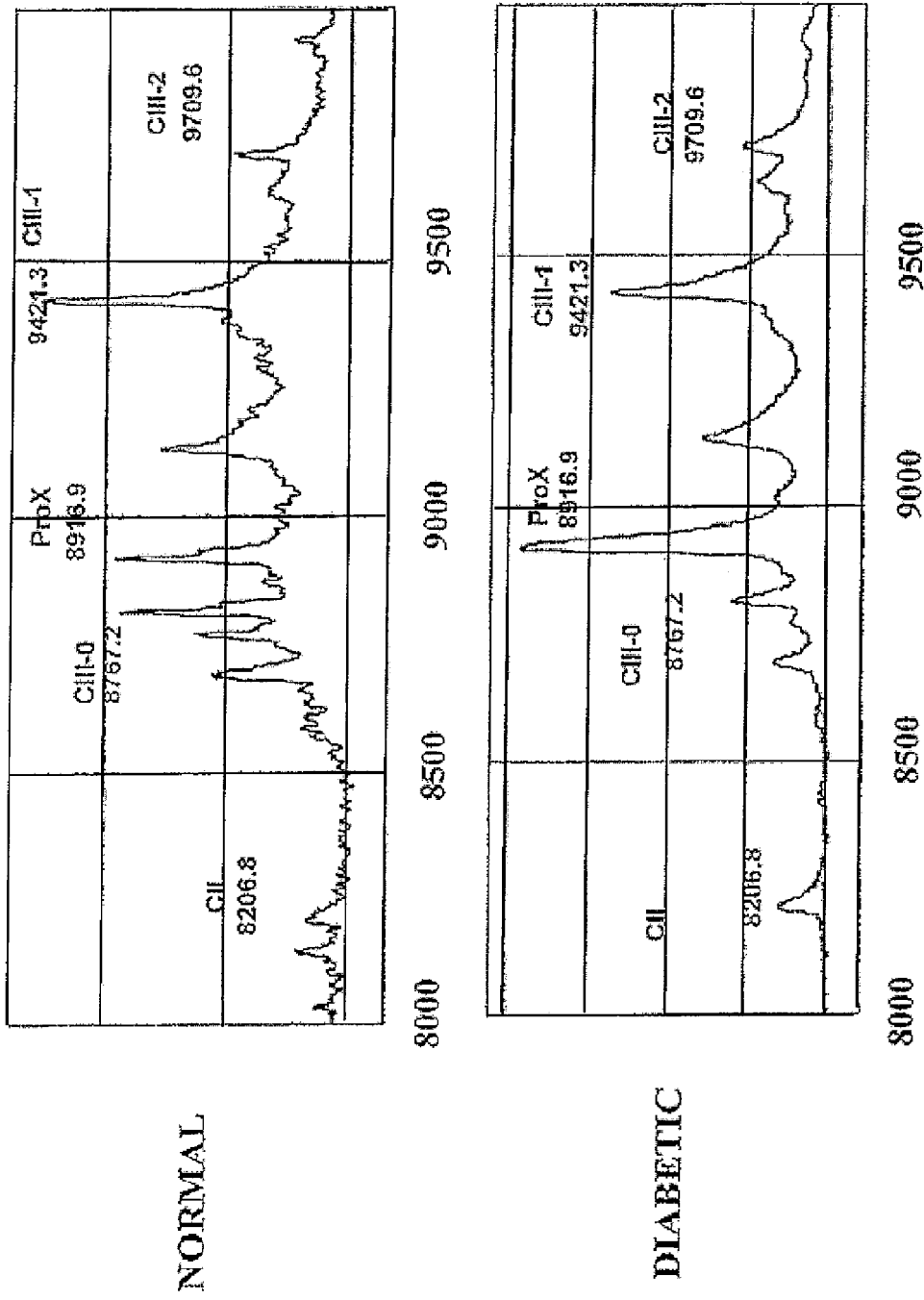
FIG. 10 is a representation of Comparison of Apolipoprotein C Profile of Normal an Diabetic Subjects.
Figure 11:
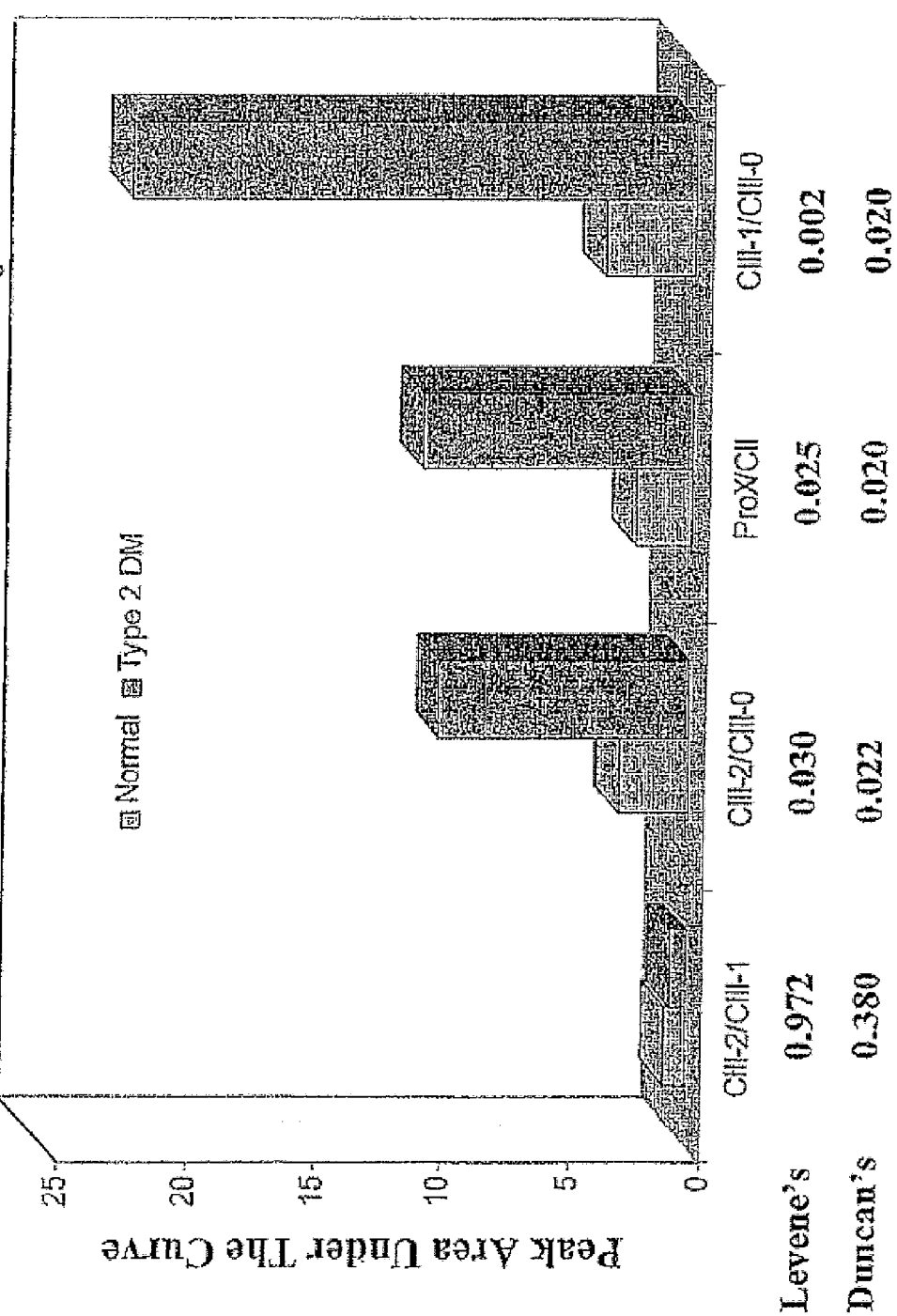
FIG. 11 is a representation of Distribution in Whole Plasma Between Normal and Diabetic Subjects.
Figure 12:
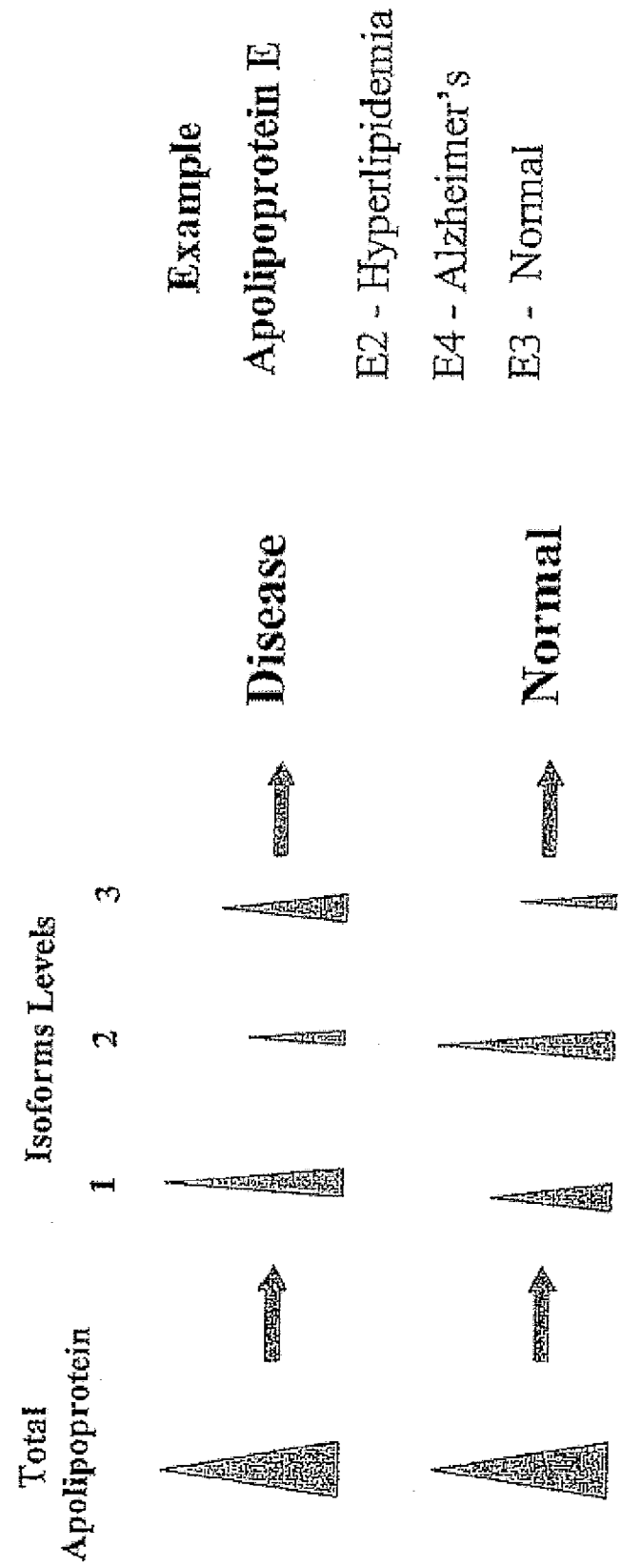
FIG. 12 is a representation of Apolipoprotein Isoform Profiles from Direct Plasma Tests.

In describing the preferred and alternate embodiments of the present invention, and with reference to FIGS. 1A-12, specific terminology is employed for the sake of clarity. The invention, however, is not intended to be limited to the specific terminology so selected, and it is to be understood that each specific element includes all technical equivalents that operate in a similar manner to accomplish similar functions.

This invention provides sensitive and rapid methods that can be useful in identifying and assessing cardiovascular diseases (e.g. lipid disorders, metabolic syndrome, and atherosclerosis), Alzheimer's disease, cancer, prostate cancer, stress, stroke, diabetes, inflammation, Parkinson's disease and other neurological disorders, and/or any condition or disorder that may be diagnosed and/or characterized using a profile comprising apolipoproteins. As an apolipoprotein profile, and relative isoform characterization, correlates with a status of a disease, so therefore the status of a disease in a patient can be determined sensitively and rapidly using the presently described technique. Thus, an ability of the presently described technique and methodology is to enable definition of disease specific apolipoprotein biomarkers or profiles and to develop quantitative assays that are rapid and useful for diagnosis or categorizing one or more diseases or conditions.

More particularly, in one illustrative embodiment, the present invention provides a method of qualifying disease status in a subject comprising the steps of:

(1) measuring at least one biomarker in a sample from the subject, wherein the at least one biomarker is selected from the group consisting of Apo CI, Apo CII, Apo CIII, Apo CIV, Apo A1, Apo A11, Apo AIV, Apo AV, Apo B100, Apo B48, Apo E, Apo D, Apo H, Apo G, Apo F, Apo J, Apo L, Apo M, isoforms thereof, and combinations thereof;

(2) analyzing or quantifying or measuring the at least one biomarker in the sample by spectrometry;

(3) preparing a profile of the at least one biomarker using the analysis, quantification, or measurement; and (4) comparing the profile of the at least one biomarker to standard profiles that indicate disease, whereby the presence, absence, or relative concentration of the at least one biomarker in the sample indicates disease.

In a related illustrative embodiment the present invention provides a method of qualifying disease status in a subject comprising the steps of:

(1) measuring a plurality of biomarkers in a sample from the subject, wherein the biomarkers are selected from the group consisting of Apo CI, Apo CIT, Apo CIII, Apo CIV, Apo A1, Apo A11, Apo AIV, Apo AV, Apo B100, Apo B48, Apo E, Apo D, Apo H, Apo G, Apo F, Apo J, Apo L, Apo M, isoforms thereof and combinations thereof;

(2) analyzing or quantifying or measuring the biomarkers in the sample by spectrometry;

(3) preparing a profile of the biomarkers using the analysis, quantification, or measurement; and (4) comparing the profile of the biomarkers to standard profiles that indicate disease, whereby the presence, absence, or relative concentration of the biomarkers in the sample indicates a disease or diseases.

In other illustrative embodiments, the measuring step comprises quantifying the amount of the at least one biomarker or plurality of biomarkers in the sample. In further illustrative embodiments, the invention involves resolution of the at least one biomarker or plurality of biomarkers, comprising the use of SELDI mass spectrometry.

Thus, the presently described high-throughput protein profiling technique, in combination with effective use of bioinformatics tools provides a useful approach to screening for biomarkers, as well as other useful benefits as compared to presently available techniques for apolipoprotein determination. The system used in the present invention preferably utilizes chromatographic PROTEINCHIPO laboratory equipment, namely, an apparatus for screening samples, detecting the presence of analytes in samples, identifying sample type, together with measuring patterns, as well as equipment for making and screening molecular arrays to assay samples using SELDI. Proteins bound to the arrays are preferably read in a PROTEINCHIPO array reader, which is a time-of-flight mass spectrometer.

Additionally, the method of this invention effectively enhances the ability of the chip to reproducibly detect modified proteins (glycosylated proteins, etc.) and degraded proteins, wherein the utilization of Protein G, Protein A, derivatives thereof, or other suitable antibody receptor molecule, facilitates accurately preferred directional placement of antibodies on the chip, wherein the term antibody, as used throughout, is intended to refer to whole antibody, antibody fragment, antibody mimic, aptimer, and/or any other suitable antigen receptor. Similarly, the term antibody receptor, as used throughout, is intended to refer to any molecular structure, or component thereof, that is able to bind with an antibody, or antigen receptor, as defined herein. Further, the method's elimination of initial extraction and targeted purification techniques coupled with the replacement of fluorescence-based detection techniques allows for the detection of a plurality of apolipoproteins with pre- and/or post-translational modifications. Pre-translational modified forms include allelic variants, slice variants and RNA editing forms. Post-translational modified forms include forms resulting from truncation, proteolytic cleavage (for example, fragments of a parent protein), glycosylation, lipidation, cysteinylation, glutationylation, phosphorylation, prenylation, acylation, acetylation, methylation, sulfation, sulfonation, hydroxylation, myristoylation, farnesylation, oxidation and ubiquitination. Modified forms of any biomarker of this invention also, themselves, may thus be used as biomarkers. Such modifications have previously served to adversely influence or prevent results in former techniques.

As may be seen, the profiles realized from the present technique may comprise the compositions, levels, and isoforms of apolipoproteins from any suitable biological matrix, such as extracted from plasma and in lipoprotein fractions, wherein such compositions, levels, and isoforms may be determinant of several diseases, disorders or conditions. As used herein, the term diseases includes disorders and conditions and is used specifically in relation to, but not limited to, cardiovascular disease and other chronic disorders such as stroke, metabolic syndrome, diabetes, Alzheimer's, HIV, inflammation, Parkinson's, neurological disease, various types of lipoproteinemia, prostate cancer, and various other cancers. For example, clinical studies conducted in conjunction with the aforementioned or other relevant diseases and the use of lipid-lowering drugs would benefit from the apolipoprotein fingerprinting technique of the present invention, wherein rapid, efficient, reliable and accurate results may be collected and analyzed. As a further example, use of the fingerprinting technique of the present invention would enable a look at the levels and distribution of apolipoproteins and their isoforms in plasma and in different lipoprotein fractions to show how these parameters change with different diseases and their treatments. For still another example, the technique of the present invention can be ideal for assessing apolipoprotein status in newborns and for evaluating apolipoprotein modifications that occur with aging, nutrition, environmental exposures, and lifestyle changes, for example.

In yet another example, the present invention provides kits for qualifying disease status in which the kits can be used to measure particular biomarkers, according to the technique present invention. For example, the kits can be used to measure any one or more of the biomarkers described herein, which biomarkers are differentially present in samples of diseased patient and normal subjects. For another example, the kits also can be used to monitor the patient's response to a course of treatment, enabling the physician to modify the treatment based upon the results of the test. For still another example, the kits can be used to identify compounds that modulate expression of one or more of the biomarkers in in vitro or in vivo animal models for diseases, assessing the impact of metabolic changes due to differences in the levels of hormones, vitamins, enzyme activities and other vital biological regulatory molecules on lipid, protein and carbohydrate metabolisms, immunity, mental health, and behavior. And, further, the kits can be used to look at the impact of genetics on nutrition, drug and other therapy, such as gene, chemo-, radio-, or the like, treatment and response, aging, behavior, growth and development, lifestyle, environment, and diseases on protein expressions and human metabolism.

One embodiment of the preferred technique of the present invention uses specific antibodies, bound to surface-enhanced chips via Protein G, to selectively absorb apolipoproteins directly from plasma samples. Protein G binds the fc portion of the antibodies, effectively and beneficially orienting the bound antibodies. Prior techniques were disadvantageously unreliably non-reproducible, wherein the physical orientation of the bound antibodies was left to chance, and thus varied in the concentration of sites that were available for subsequent binding to the target apolipoprotein. Thus, the present technique enhances the binding of the antibodies to specific antigens of interest in biological samples. In the context of the present disclosure, and particularly with respect to the antibodies as discussed hereinabove, it is noted that antibody fragments, mimics, and/or any other component comprising the appropriate variable region and/or antigen receptor may alternately be utilized.

The surface of the surface-enhanced chips retains the specific apolipoproteins, while other sample components are washed away. The EAM solution matrix facilitates laser desorption ionization of the apolipoproteins. The ionized apolipoproteins reach the detector at slightly different times based on their times of flight, which time differences can be converted to masses. The intensities of the peaks are related to the quantity of each protein. As used herein, the terms antibody and antibodies include fragments of antibodies, immunoglobulins, affybodies, etcetera. It should be noted that according to the preferred technique, and unlike other presently available techniques for apolipoprotein characterization, the profile is phenotypic, rather than genotypic. This beneficial characteristic allows for identification of modified apolipoproteins, and can therefore facilitate identification of environmental influences, for example, when comparing samples from the same individual from differing time periods. By way of further example, development of an apolipoprotein profile according to the present technique would enable identical twin samples to be distinguished based upon lifestyle modifications, or mutations, that are reflected in the profile differences.

Preferred methods of measuring the biomarkers include use of a biochip array. Biochip arrays useful in the invention include protein and nucleic acid arrays. One or more biomarkers, apolipoproteins and modifications thereof, as described herein, are captured on the biochip array and subjected to laser ionization to detect the molecular weight of the biomarkers. Analysis of the biomarkers is, for example, by molecular weight of the one or more biomarkers against a threshold intensity that is normalized against total ion current. Preferably, logarithmic transformation is used for reducing peak intensity ranges to limit the number of biomarkers detected. Also preferably, one or more internal standards are captured on the same biochip array with the biomarker unknowns, wherein the internal standard(s) is preferably a biomarker of a molecular weight of a size relevant to the biomarkers sought for profiling. The ability of the present technique to facilitate the addition of an internal standard enables quantitation of profile components, including identified apoliprotein isoforms. The ability of the described technique to define and present the contribution of each apolipoprotein isoform to overall health and relate this information to the currently measured and known total protein concentration enables the physician to translate new knowledge to existing clinical guidelines of patient care. Previous techniques have been unable to provide such data.

In preferred methods of the present invention, the step of preparing a profile of biomarkers and comparing the biomarkers with a disease status is performed by a software classification algorithm. Preferably, data is generated on immobilized subject samples on a biochip array by (1) subjecting the biochip array to laser ionization and detecting the intensity of a signal for mass/charge ratio; (2) transforming the data into computer readable form; (3) executing an algorithm that classifies the data according to user input parameters for detecting signals that represent biomarkers that are present in diseased patients and that are lacking in non-diseased subject controls; (4) comparing the levels of the biomarkers to the existing clinical reference range to assess the degree of risk or severity of the disease; and (5) transforming individual biomarker's data into the currently measured and known total protein concentration to enable the translation of new knowledge to existing clinical guidelines of patient care. Step (1) preferably uses SELDI-TOF-MS, which generally speaking comprises (a) providing a probe adapted for use with a mass spectrometer comprising an adsorbent attached thereto; (b) contacting the subject sample with the adsorbent; (c) desorbing and ionizing the biomarker or biomarkers from the probe; and (d) detecting the ionized biomarkers with the mass spectrometer.

In one example, CIPHERGEN BIOMARKER PATTERNS™ software, which is a software package for supervised classification of SELDI mass spectral data sets derived from the CIPHERGEN PROTEINCHIP® array platform mass spectrometers and chemical synthesizers used to determine protein identification and structure, is used to detect a pattern in the spectra that are generated. The data is classified using a pattern recognition process that uses a classification model. In general, the spectra will represent samples from at least two different groups for which a classification algorithm is sought. For example, the groups can be pathological versus non-pathological (for example, cancer versus non-cancer), drug responder versus drug non-responder, toxic response versus non-toxic response, progressor to disease state versus non-progressor to disease state, or phenotypic condition present versus phenotypic condition absent.

The spectra that are generated in step (1) of embodiments of the invention can be classified using a pattern recognition process that uses a classification model. In some embodiments, data derived from the spectra (for example, mass spectra or time-of-flight spectra) that are generated using samples such as "known samples" can then be used to "train" a classification model. A "known sample" is a sample that is pre-classified (for example, cancer or not cancer). Data derived from the spectra (for example, mass spectra or time-of-flight spectra) that are generated using samples such as "known samples" then can be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (for example, diseased vs. non diseased).

The training data set that is used to form the classification model may comprise raw data or pre-processed data. In some embodiments, raw data can be obtained directly from time-of-flight spectra or mass spectra, and then may be optionally "preprocessed" in any suitable manner. For example, signals above a predetermined signal-to-noise ratio can be selected so that a subset of peaks in a spectrum is selected, rather than selecting all peaks in a spectrum. In another example, a pre-determined number of peak "clusters" at a common value (for example, a particular time-of-flight value or mass-to-charge ratio value) can be used to select peaks. Illustratively, if a peak at a given mass-to-charge ratio is in less than 50% of the mass spectra in a group of mass spectra, then the peak at that mass-to-charge ratio can be omitted from the training data set. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one or more sets of relationships that define each of the known classes. New data may then be applied to the learning mechanism, which then classifies the new data using the learned relationships. Examples of super-vised classification processes include linear regression processes (for example, multiple linear regression (MLR), partial least squares (PLS) regression and principal components regression (PCR)), binary decision trees (for example, recursive partitioning processes such as CART—classification and regression trees), artificial neural networks such as back propagation networks, discriminant analyses (for example, Bayesian classifier or Fischer analysis), logistic classifiers, and support vector classifiers (support vector machines).

Once captured on a substrate, for example a biochip or antibody, any suitable method can be used to measure a biomarker or biomarkers in a sample. For example, biomarkers can be detected and/or measured by a variety of detection methods including for example, gas phase ion spectrometry methods, optical methods, electrochemical methods, atomic force microscopy and radio frequency methods. Using these methods, one or more biomarkers can be detected in the sample.

In preferred methods of the present invention, multiple biomarkers are measured. The use of multiple biomarkers increases the predictive value of the test and provides greater utility in diagnosis, toxicology, patient stratification and patient monitoring. The process called "pattern recognition" detects the patterns formed by multiple biomarkers and greatly improves the sensitivity and specificity of clinical proteomics for predictive medicine. Subtle variations in data from clinical samples, for example obtained using SELDI, indicate that certain patterns of protein expression can predict phenotypes such as the presence or absence of a certain disease, a particular stage of disease progression, or a positive or adverse response to drug treatments.[8]

Bard, et al., *Antiviral Therapy*, 11(3):361-70, 2006. Study Group Association of apolipoproteins C3 and E with metabolic changes in HIV-infected adults treated with a protease-inhibitor-containing antiretroviral therapy.

Data generation in mass spectrometry begins with the detection of ions by an ion detector as described above. Ions that strike the detector generate an electric potential that is digitized by a high speed time-array recording device that digitally captures the analog signal. The CIPHERGEN PROTEINCHIP® array system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In the CIPHERGEN PROTEINCHIPO array software, data processing typically includes TOF-to-M/Z transformation, baseline subtraction, and high frequency noise filtering. In this step, the signals are converted from the time domain to the mass domain.

Baseline subtraction improves data quantification by eliminating artificial, reproducible instrument offsets that perturb the spectrum It involves calculating a spectrum baseline using an algorithm that incorporates parameters such as peak width, and then subtracting the baseline from the mass spectrum. Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data. As disclosed above, the CIPHERGEN BIOMARKER PATTERNS™ software is preferably used to detect a pattern in the spectra that are generated. The data is classified using a pattern recognition process that uses a classification model. In general, the spectra will preferably represent samples from at least two different groups for which a classification algorithm is sought.

Samples can be collected from patients or other subjects who want to establish various disease statuses. The subjects may be particular humans who believe that they are or may be at higher risk for certain types of diseases from, for example, their medical history. Other subjects may be people who have had certain diseases and wish to monitor the effectiveness of their treatment. Further, it is possible to obtain the samples from subjects as part of routine examinations.

Any biomarker, individually, is useful in aiding in the determination of disease status. First, the selected biomarker is measured in a subject sample using the methods described herein, for example capture on a SELDI biochip followed by detection by mass spectrometry. Then, the measurement is compared with a diagnostic amount or control that distinguishes that disease status from a non-disease status. The diagnostic amount will reflect that a particular biomarker is up-regulated or downregulated in a disease status compared with a non-disease status. As is well understood in the art, the particular diagnostic amount used can be adjusted to increase sensitivity or specificity of the diagnostic assay depending on the preference of the diagnostician. The test amount as compared with the diagnostic amount thus indicates disease status.

EXAMPLE METHODOLOGIES

The example methodologies disclosed below are representative methods for using the preferred embodiments of the invention. In these methodologies, a serum sample can be collected from a patient and then fractionated using an anion exchange resin. The biomarkers in the sample are captured using an IMAC (Immobilized Metal Affinity Capture) copper PROTEINCHIP® array.[9] The biomarkers then are detected using SELDI. The results then are entered into a computer system, which contains an algorithm that is designed using the same parameters that were used in the learning algorithm and classification algorithm to originally determine the biomarkers. The algorithm produces a diagnosis based upon the data received relating to each biomarker. See FIGS. 1A-12 for experimental data regarding correlations between CIII isoforms and cardiovascular disease and diabetes. Exemplary correlations between various apolipoproteins and diseases, as previously discussed, were confirmed in the literature.[10]

[9]Dubrovsky, et al. *Clinical Chemistry*, 45(9):1675. 1999. Immobilization of monolayers of Fc-binding Receptors on Planar Solid Supports.

[10]Allard, et al. *Proteomics*, 4:2242-2004. ApoC-1 and ApoC-III as potential plasmatic markers to distinguish between ischemic and hemorrhagic stroke; Scheffer, et al., *Clinical Chemistry*. 54(8):1325-30, 2008 August. Increased plasma apolipoprotein C-III concentration independently predicts cardiovascular mortality: the Hoorn Study; Gervaise, et al. *Diabetologia*. 43(6):703-8, 2000 June. Triglycerides, apo C3 and Lp B:C3 and cardiovascular risk in type II diabetes.

The diagnosis can be determined by examining the data produced from the SELDI tests with the classification algorithm that is developed using the biomarkers. The classification algorithm depends on the particulars of the test protocol used to detect the biomarkers. These particulars include, for example, sample preparation, chip type and mass spectrometer parameters. If the test parameters change, the algorithm must change. Similarly, if the algorithm changes, the test protocol can change.

For the present preferred invention, purified apolipoproteins, plasma samples from normal subjects, and plasma samples from diabetic subjects were analyzed using the PG-20 protein chip surface. The specific apolipoproteins that were analyzed according to the method of the invention are present in a plurality of biological matrices, including, but not limited to, plasma, serum and lipoprotein fraction in various levels. The presence of each apolipoprotein is determined using antibodies specific for each of the apolipoproteins.

The below disclosed protocol is limited to the molecular weight range that can be analyzed by current MS technology. Initially, B100 (500 kD) and B48 (approx 250 kD) are either first isolated by binding to the antibody-surface, released and then chemically or enzymatically fragmented prior to MS analysis or by direct digest while bound to the PG20 chip using the below protocol.

1. Sample Preparation

Before the SELDI-TOF-MS procedure, plasma samples were diluted with buffer 5 and the antibody was coupled to the PROTEINCHIP® as follows:

Preparation of Plasma Sample:

(1) Prepare U9Buffer (9 M urea, 50 mM HEPES, 0.5% CHAPS, pH 7); and (2) Dilute plasma sample with U9 Buffer (1:2) and vortex in cold for 30 minutes.

Coupling of Antibody to PROTEINCHIP® Array (1) Dilute antibody to 0.2 mg/ml and add 2 µl to spots on array;

(2) Transfer array to a humidity chamber and incubate for 1 hour at room temperature;

(3) Aspirate antibody without touching surface of spot;

(4) Wash chip in 15 mL conical tube for 10 minutes with 8 mL of wash buffer;

(5) Empty and wash with 8 mL of phosphate-buffered saline for 5 minutes, and repeat; and (6) Blot excess PBS from the surface of the chip.

2. SELDI-TOF-MS Procedure (1) Add 2 µl of plasma sample to each spot;

(2) Transfer array to a humidity chamber and incubate for 1 hour at room temperature;

(3) Wash chip in 15 mL conical tube with 8 mL of wash buffer for 10 minutes;

(4) Empty and wash with 8 mL of Phosphate-buffered Saline for 5 minutes, and repeat;

(5) Empty and wash with 8 mL of 1 mM HEPES (N-2-Hydroxyethylpiperazine-N'-2-Ethanesulfonic Acid) 1 minute, and repeat;

(6) Remove chip from tube, flick off liquid, and air-dry for 10 minutes;

(7) Prepare EAM solution by adding 100 µl of 99.8% acetonitrile and 100 µl of 1.0% trifluoroacetic acid to 1 vial (10 mg) of sinapinic acid powder, and vortex for 5 minutes to dissolve the powder; and (8) Add 5 µl of EAM solution to each spot and air dry for 5 minutes, repeat, and air dry for 10 minutes.

The procedure may be modified for use with a bioprocessor that allows larger volumes and automated addition of samples and reagents. Both positive and negative controls are usually included in experiments. TNF-a (Tumor Necrosis Factor Alpha) antibody and antigen are included in the kit for this purpose.

3. Generation of Fingerprints

The preferred procedure for generating apolipoprotein fingerprints for plasma samples and purified apolipoproteins is described below:

(1) The PROTEINCHIP® array reader and software (Ciphergen Biosystems, Inc.) are used to generate the profiles.

(2) Spot protocols are generated and used to make the chips.

(3) Data collection parameters must be adjusted for each antigen and are based on molecular mass. Instructions are included in the PROTEINCHIP® array Antibody Capture Kit supplied by Ciphergen Biosystems, Inc.

(4) The data was analyzed and the apolipoprotein fingerprints were generated by, for example, comparing the data intrinsically with itself and comparing the data extrinsically with norms such as, for example, control subjects.

Alternatively, this invention can be carried out by coupling antibodies, fragments thereof, or mimic molecules to beads, capturing the apolipoproteins on the beads, eluting purified proteins from the beads, and then detecting by any version of mass spectrometry, including matrix assisted laser desorption ionization (MALDI) and electrospray methods. Methods for coupling antibodies to beads are well known in the art and such methods are suitable for the present invention. MALDI is a laser-based soft ionization method in which the sample is embedded in a chemical matrix that greatly facilitates the production of intact gas-phase ions from large, nonvolatile, and thermally labile compounds such as proteins, oligonucleotides, synthetic polymers, and large inorganic compounds. The matrix plays a key role in this technique by absorbing the laser light energy and causing a small part of the target substrate to vaporize.

The foregoing detailed description of the preferred embodiments and the appended figures have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

Again, although the description given above includes specific examples of currently envisioned embodiments of the present invention, these possibilities should not be understood as limiting the scope of the present invention but rather as providing illustrations of some of the embodiments that are now preferred. Several examples of alternate embodiments are also described and various other alternatives, adaptations, and modifications may be made within the scope of the present invention. Merely listing or numbering the steps or blocks of a method, procedure, or experiment in a certain order does not constitute any limitation on the order of the steps of that method. Many modifications and other embodiments of the invention will come to mind to one skilled in the art to which this invention pertains having the benefit of the teachings presented in the foregoing descriptions and the associated drawings. Although specific terms may be employed herein, they are used in a generic and descriptive sense only and not for purposes of limitation. Accordingly, the claims that follow herein and their legal equivalents, rather than the examples given in the specification, should determine the scope of present.

What is claimed is:

1. A method for obtaining and reporting a profile of at least one selected apolipoprotein biomarker in a biological sample, comprising: a) obtaining the biological sample; b) treating a surface with an antibody receptor molecule; c) applying at least one antigen receptor to the treated surface to bind with the bound antibody receptor molecule, said at least one antigen receptor specific for apolipoprotein biomarker; d) applying the biological sample directly to the treated surface to bind with the at least one selected apolipoprotein biomarker isoform profile; e) removing unbound components of the biological sample; f) measuring said apolipoprotein biomarker profile, by directly analyzing the sample by spectrometry; and g) preparing the profile using the simultaneous analysis wherein the said apolipoprotein biomarker profile comprises Apo CI, Apo CII, Apo CIII, Apo CIV, Apo A1, Apo A11, Apo AIV, Apo AV, Apo B48, Apo B100, Apo D, Apo E, Apo F, Apo G, Apo H, Apo J, Apo L and Apo M.

2. The method as claimed in claim 1, wherein said apolipoprotein biomarker profile further comprises, profiles of isoforms, modifications, mutations, and combinations thereof in biological matrices.

3. The method as claimed in claim 1, wherein the simultaneous analysis is any version of mass spectrometry, producing a quantitative and qualitative profile of the apolipoprotein isoforms and derivatives from the biological sample.

4. The method as claimed in claim 1, wherein the profile is a quantitative and qualitative profile of apolipoproteins and derivatives directly from the biological sample, and whereby at least one disease may be identified from the profile.

5. The method as claimed in claim 1, wherein the biological sample is selected from the group consisting of human biological matrices, urine, plasma, serum, and human lipoprotein fractions.

6. The method as claimed in claim 4, wherein the at least one disease is selected from the group consisting of diabetes, stroke, stress, Alzheimer's, cardiovascular diseases, lipid disorders, metabolic syndrome, obesity, inflammation, Parkinson's disease, neurological disorders, and atherosclerosis.

7. The method of claim 1 for further determining the concentration of specific apolipoproteins directly in a biological sample, the sample being obtained from a patient and the sample including plasma, serum, and lipoprotein fractions, the method further comprising the steps of: adding a specific volume of an internal standard to the sample; applying the sample to a surface-enhanced, Protein G-coated, antibody-bound chip; determination of the concentration of the apolipoproteins profiles using a value of the internal standard.

8. The method as claimed in claim 7, wherein each analyzed apolipoprotein is bound to a specific antibody on the chip.

9. The method as claimed in claim 8, wherein the specific antibodies are immobilized on the antibody capture protein coated surface of the chip, and wherein the specific antibodies are selected from the group consisting of antibody fragment, antibody mimic, antibody, and aptamer.

10. The method as claimed in claim 9 wherein the sample is applied to an allowed to bind with the antibody capture protein coated surface, and the unbound sample components are washed away.

11. The method as claimed in claim 7, wherein the mass spectrometry is laser desorption ionization time-of-flight mass spectrometry.

12. The method as claimed in claim 7, wherein apolipoproteins are selected from the group consisting of Apo CI, Apo CII, Apo CIII, Apo CIV, Apo Al, Apo All, Apo AIV, Apo AV, Apo B48, Apo B100, Apo D, Apo E, Apo F, Apo G, Apo H, Apo J, Apo L, and Apo M and the chip bound antibodies are selected from the group consisting of antibodies to Apo CI, Apo CII, Apo CIII, Apo CIV, Apo Al, Apo All, Apo AIV, Apo AV, Apo B48, Apo B100, Apo D, Apo E, Apo F, Apo G, Apo H, Apo J, Apo L, and Apo M.

13. The method as claimed in claim 12, wherein the sample is selected from the group consisting of human urine, body fluid, plasma, serum, and human lipoprotein fractions.

14. The method as claimed in claim 7, wherein the at least one internal standard protein is developed by modifying at least one selected purified protein, wherein a reference value is set for each at least one internal standard protein using high resolution mass spectrometry, and wherein concentration value for each at least one selected apolipoprotein biomarker identified in the biological sample are based on internal standards developed by modifying selected purified proteins and defining reference values therefore using high resolution mass spectrometry.

15. The method as claimed in claim 2, wherein the modifications are selected from the group consisting of glycation, sialylation, fragmentation, amino acid substitutions, allelic variants, slice variants, RNA editing forms, pre-translational modifications, post-translational modifications, truncation, proteolytic cleavage, glycosylation, lipidation, cysteinylation, glutationylation, phosphorylation, prenylation, acylation, acetylation, methylation, sulfation, hydroxylation, myrisotylation, farnesylation, oxidation, and ubiquitination.

16. The method of claim 1 for further use in assessing risk factors, disease state, drug treatment and response in the field of pharmacogenetics, the method further comprising the steps of:
    collecting a first biological specimen from a human being, or utilizing a previously obtained biological specimen as a first biological specimen; generating a first apolipoprotein fingerprint profiles from biological specimen, said apolipoprotein fingerprint comprising data on presence and absence of a plurality of targeted apolipoproteins, on structural features and differences between isoform profiles of said plurality of targeted apolipoproteins, and on concentration of said plurality of targeted apolipoproteins;
    comparing said first apolipoproteins fingerprint profiles data to reported risk factor data to assess risk factors, or to reported disease state data to assess disease state or status;

collecting a second biological specimen from the same human being;
generating a second apolipoprotein fingerprint; and
comparing said second apolipoprotein fingerprint data with said first apolipoprotein fingerprint data to assess drug treatment and response, where said second biological specimen is collected after a drug treatment.

17. A method for obtaining a profile of a plurality of selected apolipoprotein biomarkers in a biological sample from a subject, comprising the steps of:
a) obtaining the biological sample from a subject;
b) applying the biological sample to the surface of a capture reagent that specifically captures the plurality of selected apolipoprotein biomarkers, allowing the plurality of selected apolipoprotein biomarkers to bind to the capture reagent, and removing unbound sample components;
c) simultaneously analyzing the captured plurality of selected apolipoprotein biomarkers by mass spectrometry; and
d) preparing the profile using the analysis results, wherein the plurality of selected apolipoprotein biomarkers comprises Apo CI, Apo CII, Apo CIII, Apo CIV, Apo AI, Apo AII, Apo AIV, Apo AV, Apo B48, Apo B100, Apo D, Apo E, Apo F, Apo G, Apo J, Apo L, Apo M, isoforms thereof, and combinations thereof.

18. The method as claimed in claim 17, further comprising the step of: using the profile to diagnose a disease in the subject, where the disease is selected from the group consisting of cancer, diabetes, stroke, stress, Alzheimer's disease, cardiovascular disease, inflammation, Parkinson's disease, neurological disorders, lipid disorders, metabolic syndrome, and atherosclerosis.

19. The method as claimed in claim 1, wherein the step of applying at least one antigen receptor to the treated surface with bound antibody receptor molecule further comprises applying at least two antigen receptors distinguishable at least by molecular mass relative to each other, to the treated surface to bind with the antibody receptor molecule, wherein the antibody receptor molecule is selected from the group consisting of a specifically designed apolipoprotein antibody, an antibody analog, and an antibody mimic molecule;
adding at least one internal standard protein to bind with at least one of the available antigen receptors having a known molecular mass;
measuring the internal standard protein coincident with measuring the at least one selected apolipoprotein biomarker profiles by directly analyzing the sample by spectrometry; and
directly and simultaneously quantifying the at least one selected apolipoprotein biomarker profile in the same biochips by comparing the internal standard.

20. The method as claimed in claim 7, further comprising the steps of identifying isoforms and the relative quantitative concentrations thereof to generate direct isoform profile diagnostic tool, wherein the isoform profile diagnostic tool may detect cancer, prostate cancer, diabetes, stroke, stress, Alzheimer's, cardiovascular diseases, lipid disorders, metabolic syndrome, obesity, Parkinson's disease, neurological disorders, inflammation, and atherosclerosis.

21. The method of claim 16, wherein the drug treatment assessed is a lipid-lowering drug, and wherein parameters comprising levels and distribution of apolipoproteins their isoforms profiles and modifications profiles may be monitored for change.

22. An assay for individualization, differentiation and relative quantification of a mixture comprising apolipoprotein isoforms that indicate a patient status, comprising the steps of:
a) preparing a surface with an antibody reactive molecule;
b) applying a plurality of apolipoprotein antibodies to said surface to bind with said antibody reactive molecule;
c) applying a mixture of apolipoprotein isoforms from a patient to bind with said said plurality of apolipoprotein antibodies, wherein said mixture of apolipoprotein isoforms may be non-purified and said plurality of apolipoprotein antibodies may be any molecular fragment adapted to bind as an apolipoprotein antibody to said mixture of apolipoprotein isoforms;
d) generating a phenotypic isoform profile of said mixture of apolipoprotein isoforms; and
e) utilizing said phenotypic isoform profile for identification of status of the patient relative to a disease or condition, for identification of a compromised physiological process, or for definition of one or more disease specific apolipoprotein biomarkers or profiles.

23. The assay of claim 22, wherein said plurality of apolipoprotein antibodies is Apo CIII isoform antibodies, wherein identification of high Apo CIII-0 levels in said profile correlates to insulin resistance and to beta cell function, and wherein identification of changes in the proportions of Apo CIII isoforms in said profile correlates with the progression and differentiation between Hypertriglyceridemia, Metabolic Syndrome and Type 2 Diabetes.

24. The assay of claim 22, wherein said apolipoproteins profiled and the relevant disease or condition status identified thereby comprise Apo D for Alzheimer's disease, Apo B for cardiovascular disease.

25. The assay of claim 22, wherein the disease or condition status identified by said phenotypic isoform profile comprise cardiovascular disease, stroke, metabolic syndrome, diabetes, Alzheimer's, HIV and HIV patients under protease inhibitors (hypertriglyceridemic), and various types of lipoproteinemia.

26. The assay of claim 22, wherein the plurality of apolipoprotein fingerprint profile or phenotypic isoform profile status is assessed in newborns.

27. The assay of claim 22, wherein said phenotypic isoform profiles provide data for evaluating apolipoprotein modifications that occur with aging, nutrition, environmental exposures, and lifestyle changes.

28. The assay of claim 22, wherein said apolipoproteins profiled and the relevant compromised physiological process identified thereby comprise Apo J for sperm maturation, Apo J for lipid transportation, Apo J for complement inhibition, Apo J for tissue remodeling, Apo J for membrane recycling, Apo J for cell-cell and cell-substratum interactions, Apo J for stabilization of stressed proteins in a folding-competent state, Apo J for promotion or inhibition of apoptosis, Apo H for blood coagulation, Apo H for prothrombinase activity of activated platelets, Apo F for cholesterol ester transfer protein (CETP) activity, Apo F for cholesterol transport regulation, and Apo M for lipid transport.

29. The assay of claim 22, wherein an internal standard is added, detected, and measured with said mixture of apolipoprotein isoforms, wherein said internal standard is a known protein with very similar antibody-binding properties to the apolipoproteins of interest but with a visibly different molecular mass.

30. The assay of claim 22, wherein separation, concentration and detection of said apolipoprotein isoforms is accomplished on one biochip.

31. The assay of claim 30, wherein said biochip is subjected to laser ionization, the intensity of a signal is detected for mass/charge ratio, the resulting data is transformed into a computer readable form, and an algorithm is executed that classifie said data according to a plurality of user input parameter groups for detecting signals that represent biomarkers present in diseased patients and that are lacking in non-diseased subject controls, based upon changes in a native analyte concentration profile relative to a disease state profile selected from the group, consisting of a new apolipoprotein or new modified apolipoprotein species with its plurality of isoforms, and a plurality of isoform modifications.

32. The assay of claim 31, wherein said input parameter groups are selected from groups consisting of pathological versus non-pathological, drug responder versus drug non-responder, toxic response versus non-toxic response, progressor to disease state versus non-progressor to disease state, or phenotypic condition present versus phenotypic condition absent.

* * * * *